United States Patent
LaRosa et al.

(10) Patent No.: US 11,116,780 B2
(45) Date of Patent: Sep. 14, 2021

(54) TOPICAL ANALGESIC

(71) Applicant: Concept Matrix Solutions, Woodland Hills, CA (US)

(72) Inventors: Tony LaRosa, Woodland Hills, CA (US); Robert Davidson, Woodland Hills, CA (US); David Reid, Woodland Hills, CA (US)

(*) Notice: Subject to any disclaimer, the term of this patent is extended or adjusted under 35 U.S.C. 154(b) by 20 days.

(21) Appl. No.: 16/928,664

(22) Filed: Jul. 14, 2020

(65) Prior Publication Data

US 2021/0015836 A1   Jan. 21, 2021

Related U.S. Application Data

(60) Provisional application No. 62/875,583, filed on Jul. 18, 2019, provisional application No. 62/907,749, filed on Sep. 30, 2019, provisional application No. 62/977,851, filed on Feb. 18, 2020, provisional application No. 62/987,080, filed on Mar. 9, 2020.

(51) Int. Cl.

| | |
|---|---|
| *A61K 31/7034* | (2006.01) |
| *A61K 31/045* | (2006.01) |
| *A61K 31/05* | (2006.01) |
| *A61K 31/522* | (2006.01) |
| *A61K 47/02* | (2006.01) |
| *A61K 47/12* | (2006.01) |
| *A61K 47/22* | (2006.01) |
| *A61K 47/24* | (2006.01) |
| *A61K 47/32* | (2006.01) |
| *A61K 9/00* | (2006.01) |
| *A61K 9/06* | (2006.01) |
| *A61K 47/44* | (2017.01) |

(52) U.S. Cl.
CPC ........ *A61K 31/7034* (2013.01); *A61K 9/0014* (2013.01); *A61K 9/06* (2013.01); *A61K 31/045* (2013.01); *A61K 31/05* (2013.01); *A61K 31/522* (2013.01); *A61K 47/02* (2013.01); *A61K 47/12* (2013.01); *A61K 47/22* (2013.01); *A61K 47/24* (2013.01); *A61K 47/32* (2013.01); *A61K 47/44* (2013.01)

(58) Field of Classification Search
CPC .. A61K 31/7034; A61K 31/05; A61K 31/045; A61K 31/522; A61K 47/32; A61K 9/06; A61K 47/44; A61K 47/02; A61K 47/12; A61K 47/22; A61K 9/0014; A61K 47/24
USPC .......................................................... 514/35
See application file for complete search history.

(56) References Cited

U.S. PATENT DOCUMENTS

| | | | |
|---|---|---|---|
| 7,282,224 B1 * | 10/2007 | Roederer | A61K 31/165 424/725 |
| 2017/0290870 A1 * | 10/2017 | Schaneville | A61K 9/006 |
| 2019/0247299 A1 * | 8/2019 | Cameron | A61K 36/28 |

OTHER PUBLICATIONS

Abdulbaqi et al. Ethosomal nanocarriers: the impact of constituents and formulation techniques on ethosomal properties, in vivo studies, and clinical trials. International Journal of Nanomedicine 11:2279-2304, 2016. (Year: 2016).*

* cited by examiner

*Primary Examiner* — Yih-Horng Shiao
(74) *Attorney, Agent, or Firm* — Gary J. Speier; Carlson, Caspers, Vandenburgh & Lindquist, P.A.

(57) ABSTRACT

Provided herein is a topical analgesic composition that includes an external analgesic agent, one or more pharmaceutically acceptable excipients, and at least one of a cannabinoid, terpene, and flavonoid. Also provided is a method that includes topically administering to a skin surface of a subject (e.g., human) the topical analgesic composition.

20 Claims, No Drawings

TOPICAL ANALGESIC

RELATED U.S. APPLICATION DATA

This application claims priority to provisional patent application No. 62/875,583 filed on Jul. 18, 2019, provisional patent application No. 62/907,749 filed Sep. 30, 2019, provisional patent application No. 62/977,851 filed Feb. 18, 2020; and provisional patent application No. 62/987,080 filed Mar. 30, 2020, the contents of which are incorporated by reference herein in their entirety.

SUMMARY OF THE INVENTION

The present invention provides for a topical analgesic composition that includes an external analgesic agent, one or more pharmaceutically acceptable excipients, and at least one of a cannabinoid, terpene, and flavonoid.

The present invention also provides for a topical analgesic composition that includes an external analgesic agent, solvent, emulsifier, polymeric binder, solubility oil, antioxidant, preservative, herbal active ingredient, microcirculation stimulant, pH adjusting agent, and at least one of a cannabinoid, terpene, and flavonoid.

The present invention also provides for a topical analgesic cream that includes menthol, cannabidiol (CBD), carbopol, hydroxylated lecithin, caffeine anhydrous, salicin, organic hemp oil, sodium benzoate, tocopheryl acetate, sodium bicarbonate, and water.

The present invention also provides for a topical analgesic cream that includes 2.5±0.5 wt. % menthol, 0.35±0.1 wt. % cannabidiol (CBD), 1.4±0.3 wt. % carbopol 980 NF, 2±0.4 wt. % hydroxylated lecithin, 1.5±0.3 wt. % caffeine anhydrous, 1.25±0.25 wt. % salicin (98 wt. % pure), 1±0.2 wt. % organic hemp oil, 0.1±0.02 wt. % sodium benzoate, 0.1±0.02 wt. % tocopheryl acetate, 1.5±0.3 wt. % sodium bicarbonate, and 88.30±5 wt. % water.

The present invention also provides for a topical analgesic cream that includes 2.5±0.5 wt. % menthol, 0.32±0.1 wt. % cannabidiol (CBD), 1.4±0.3 wt. % carbopol 980 NF, 2±0.4 wt. % hydroxylated lecithin, 1.5±0.3 wt. % caffeine anhydrus, 1.25±0.25 wt. % salicin (98 wt. % pure), 1±0.2 wt. % organic hemp oil, 0.1±0.02 wt. % sodium benzoate, 0.1±0.02 wt. % tocopheryl acetate, 1.5±0.3 wt. % sodium bicarbonate, and 88.33±5 wt. % water.

The present invention also provides for a method that includes topically administering to a skin surface of a subject (e.g., human) the topical analgesic composition described herein.

The present invention also provides for a method that includes topically administering to a skin surface of a subject (e.g., human) the topical analgesic composition described herein to treat, prevent, ameliorate, or manage at least one of: (i) simple backache, (ii) sore muscles, (iii) muscle fatigue, (iv) muscle stiffness, (v) joint stiffness, (vi) arthritis, (vii) muscle strains, (viii) bursitis, (ix) tendonitis, (x) bruises, (xi) contusion, (xii) cramps, and (xii) sprain.

The present invention also provides for a method that includes topically administering to a skin surface of a subject (e.g., human) the topical analgesic composition described herein to provide for the temporary relief from at least one of: (i) simple backache, (ii) sore muscles, (iii) muscle fatigue. (iv) muscle stiffness, (v) joint stiffness, (vi) arthritis, (vii) muscle strains, (viii) bursitis, (ix) tendonitis, (x) bruises, (xi) contusion, (xii) cramps, and (xii) sprain.

The present invention also provides for a method that includes topically administering to a skin surface of a subject (e.g., human) the topical analgesic composition described herein to: provide a cooling sensation, provide a cooling pain relief, provide a warming pain relief, provide a warming sensation, provide a cooling pain relief, to provide temporary relief of minor aches and pains of muscles and joints, to soothe muscle aches, to alleviate discomfort resulting from strenuous athletic training, to aid in recovery from strenuous athletic training, to numb away the pain, to provide pain management, and/or to desensitize aggravated nerves.

The present invention also provides for a method of manufacturing a topical analgesic composition described herein. The method includes: (a) dissolving CBD in hemp oil to obtain a hemp mixture; (b) contacting menthol, caffeine anhydrous, white willow bark extract (salicin 98), sodium benzoate, and tocopheryl (or tocopheryl acetate) to obtain a dry mixture; (c) contacting carbopol 980 NF and water until the carbopol 980 NF is dissolved in the water or is dispersed throughout the water, to obtain a carbopol mixture; (d) contacting lecithin, water, and the dissolved CBD to form a first mixture; (e) contacting the hemp mixture, the dry mixture, and the carbopol mixture to form a second mixture; (f) contacting sodium bicarbonate and the second mixture.

DETAILED DESCRIPTION

Compositions of the present invention may be beneficial in preventing, treating, managing, and/or ameliorating a variety of minor aches and pains of muscles. Specifically, the compositions may be beneficial in preventing, treating, managing, and/or ameliorating at least one of: (i) simple backache, (ii) sore muscles, (iii) muscle fatigue, (iv) muscle stiffness, (v) joint stiffness, (vi) arthritis, (vii) muscle strains, (viii) bursitis, (ix) tendonitis, (x) bruises, (xi) contusion, (xii) cramps, and (xii) sprain. More specifically, the compositions may be beneficial by providing a cooling sensation, cooling pain relief, warming pain relief, warming sensation, or cooling pain relief; to soothe muscle aches, alleviate discomfort resulting from strenuous athletic training, aid in recovery from strenuous athletic training, numb away the pain, provide pain management, and/or desensitize aggravated nerves.

In another aspect, the invention relates to a method of preventing, treating or ameliorating minor aches and pains of muscles. The method includes administering to a person suffering from at least one of said conditions (or is at risk thereof), an effective amount of one or more compositions as described herein.

The compositions of the present invention include at least one of a cannabinoid, terpene, and flavonoid. Without wishing to be limited to any particular theory, it is currently believed that the cannabinoid, terpene, and/or flavonoid provides stability to the composition, which serves to prevent phase separation of an aqueous and a lipid phase in the composition at elevated temperatures (e.g. temperatures of more than about 25° C.), which might promote improved or prolonged contact to the skin, resulting in the observed increased retention times of the active(s) in the dermis and epidermis.

Across multiple topical dosage forms (e.g., creams, gels, lotions, ointments, foams, etc.) the cannabinoid, terpene, and/or flavonoid can be present in an amount, such that it exhibits activity as an active ingredient for the intended purpose (e.g., analgesic). In doing so, the cannabinoid, terpene, and/or flavonoid may further have a synergistic effect with the active ingredient(s) present therein. In other embodiments, the cannabinoid, terpene, and/or flavonoid can be present in sub-therapeutic amounts.

It is currently believed that the topical use of the cannabinoid, terpene, and/or flavonoid provides additional benefits, which include: smoothing skin, strengthening underlying epidermal tissue, removing dead skin cells, balancing oil production, and helping the skin retain moisture levels. It is further believed that the cannabinoid, terpene, and/or flavonoid helps cleanse and moisturize the skin. Healthy skin is just like any other organ in your body: It continuously needs oxygen and nutrients to be brought to the cells, and toxins need to be washed away. It is further believed that the cannabinoid, terpene, and/or flavonoid contributes to the optimal skin health while leaving skin feeling and looking youthful.

It is also currently believed that some consumers have a preference to use a topical skin product that is environmentally friendly to produce and includes fewer toxic chemicals that are otherwise put into the environment when creating topical skin products. Inclusion of substances, such as cannabinoid, terpene, and/or flavonoid (which are natural products), are viable options for such consumers.

Definitions

The term "topical analgesic composition" refers to a topical composition containing an external analgesic agent, various inactive ingredients or excipients, and at least one of a terpene and cannabinoid. The composition is suitable for the therapeutic topical treatment of minor aches and pains of muscles.

The term "muscle pain" or "muscle ache" refers to a pain caused by tension, stress or overuse of a muscle. Muscle pain can be due to or caused by simple backache, sore muscles, muscle fatigue, muscle stiffness, joint stiffness, arthritis, muscle strains, bursitis, tendonitis, bruises, contusion, cramps, and sprain.

The term "external analgesic agent" or "analgesic agent" refers to any chemical and/or drug that when topically administered at the site of muscle pain or ache, effectively treats and/or leads to a visible reduction of symptoms associated with sore or fatigued muscles, arthritis, tendonitis, cramps or sprain. Representative analgesic agents include, for example aspirin, benzocaine, benzyl alcohol, butamben picrate, camphor, camphor (when combined with phenol), camphorated metacresol, capsaicin, chloral hydrate, chlorobutanol, cyclomethycaine sulfate, dibucaine, dibucaine hydrochloride, dimethisoquin hydrochloride, diphenhydramine hydrochloride, dyclonine hydrochloride, eugenol, hexylresorcinol, hydrocortisone, hydrocortisone (0.25-1%), hydrocortisone acetate, hydrocortisone acetate (0.25-1.0%), juniper tar, lidocaine, lidocaine hydrochloride, menthol, methapyrilene hydrochloride, methyl salicylate, obtundia surgical dressing, phenol, phenolate sodium, pramoxine hydrochloride, resorcinol, salicylamide, tetracaine, tetracaine hydrochloride, thymol, tripelennamine hydrochloride, trolamine salicylate. The topical analgesic compositions described herein include one or more external analgesic agents.

The term "solvent" refers to a substance, typically a liquid at ambient conditions, capable of dissolving another substance (a solute), resulting in a solution. When one substance is dissolved into another, a solution is formed. This is opposed to the situation when the compounds are insoluble like sand in water. In solution, all of the ingredients are uniformly distributed at a molecular level and no residue remains. The mixing is referred to as miscibility, whereas the ability to dissolve one compound into another is known as solubility. However, in addition to mixing, both substances in the solution interact with each other. When something is dissolved, molecules of the solvent arrange themselves around molecules of the solute. Heat is involved and entropy is increased making the solution more thermodynamically stable than the solute alone. This arrangement is mediated by the respective chemical properties of the solvent and solute, such as hydrogen bonding, dipole moment and polarizability. The topical analgesic compositions described herein can optionally include one or more solvents.

The term "emulsifier" refers to a substance capable of forming or promoting an emulsion. An emulsion is a mixture of two or more liquids that are normally immiscible (non-mixable or unblendable). Emulsions are part of a more general class of two-phase used systems of matter called colloids. Although the terms colloid and emulsion are sometimes interchangeable, emulsion should be used when both the dispersed and the continuous phase are liquids. In an emulsion, one liquid (the dispersed phase) is dispersed in the other (the continuous phase). Examples of emulsions include vinaigrettes, milk, mayonnaise, and some cutting fluids for metal working. The photo-sensitive side of photographic film is an example of a colloid. The topical analgesic compositions described herein can optionally include one or more emulsifiers.

The term "polymeric binder" refers to a substance that draws other materials together to form a cohesive whole chemically or mechanically by adhesion or cohesion. This can introduce cross-links between molecules that affect the thickness or viscosity of the topical analgesic composition/cream. Examples of polymeric binders include Carbopol 90, carbomer, cetyl alcohol, stearic acid, carnauba wax, hydroxyethyl cellulose, guar gum, xanthan gum, gelatin, magnesium aluminum silicate, silica, bentonite, cetyl palmitate, ammonium acryloyldimethyltaurate, cetearyl alcohol, glucose-D, hectorite gel, stearyl palmitate, gum arabic, hydroxypropyl starch phosphate, tapioca starch, acrylates octylacrylamide copolymer, carbomer 940, polyamide 3, castor wax, hydroxypropyl methylcellulose, *Caesalpinia spinosa* gum, *brassica* alcohol, carbomer 980 QD, sodium stearate, polyhydroxystearic acid, tribehenin, arrowroot starch, rice starch, candelilla wax, beeswax, ozokerite wax, sunflower wax, PEG-150 distearate, polyacrylate crosspolymer-6, acrylates C10-30 alkyl acrylate crosspolymer, hydroxypropyl guar, and cyclopentasiloxane (silicone gel). The topical analgesic compositions described herein can optionally include one or more polymeric binders.

The term "solubility oil" refers to oil or lipid composition that aids in the solubilization of cannabinoids, cannabinoid isolates, or CBD isolate. An example of solubility oil is organic hemp oil, which contains nutrients and lipids such as vitamin E, omega-6 and omega-3 fatty acids, polyunsaturated fatty acids and proteins. Hemp oil is extracted from hemp seeds, which do not contain cannabinoids or CBD. The topical analgesic compositions described herein can optionally include one or more solubility oils.

The term "thickening agent" or "viscosity-increasing agent" refers to a substance which can increase the thickness or viscosity of a liquid without substantially changing its other properties. Some thickening agents are gelling agents (gellants), forming a gel, dissolving in the liquid phase as a colloid mixture that forms a weakly cohesive internal structure. Others act as mechanical thixotropic additives with discrete particles adhering or interlocking to resist strain. Typical gelling agents include natural gums, starches, pectins, agar-agar and gelatin. Often they are based on polysaccharides or proteins. Examples include: Alginic acid, sodium alginate, potassium alginate, ammonium alginate, calcium alginate—polysaccharides from brown algae; Agar (polysaccharide obtained from red algae); Carrageenan (polysaccharide obtained from red seaweeds); Locust bean gum (natural gum polysaccharide from the seeds of the carob tree); Pectin (polysaccharide obtained from apple or citrus-fruit); and Gelatin (made by partial hydrolysis of animal collagen). The thickening agent or viscosity-increasing agent also includes cellulose thickeners, such as e.g., hydroxypropyl cellulose, hydroxyethyl cellulose, hydroxypropyl cellulose, hydroxypropyl methyl cellulose, methyl cellulose, carbopols, polyacrylic acid, and polyvinyl alcohol. The topical analgesic compositions described herein can optionally include one or more thickening agents.

The term "emollient" refers to lubricating ingredients (i.e., fats, phospholipids and sterols) that soften and smooth skin while helping it to retain moisture. Emollients are typically nonpolar and can come from natural or synthetic sources in the form of plant oils, mineral oils, shea butter, cocoa butter, petrolatum, cholesterol, silicones or animal oils (including emu, mink and lanolin). The topical analgesic compositions described herein can optionally include one or more emollients.

The term "cannabinoid" refers to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid Δ9-tetrahydrocannabinol (THC), the primary psychoactive compound of *Cannabis*. Cannabidiol (CBD) is another major constituent of the plant, representing up to 40V % in extracts of the plant resin. There are at least 85 different cannabinoids isolated from *Cannabis*, exhibiting varied effects. The cannabinoid can be synthetically prepared, or alternatively, can be obtained naturally (e.g., from plant matter). Either way, the cannabinoid can have the requisite purity (e.g., at least 95 wt. % pure, at least 98 wt. % pure, at least 99 wt. % pure, or at least 99.5 wt. % pure).

| Cannabinoids isolated from *Cannabis* |
|---|
| 1. Cannabigerol ((E)-CBG-C5) |
| 2. Cannabigerol monomethyl ether ((E)-CBGM-C5 A) |
| 3. Cannabinerolic acid A ((Z)-CBGA-C5 A) |
| 4. Cannabigerovarin ((E)-CBGV-C3) |
| 5. Cannabigerolic acid A ((E)-CBGA-C5 A) |
| 6. Cannabigerolic acid A monomethyl ether ((E)-CBGAM-C5 A) |
| 7. Cannabigerovarinic acid A ((E)-CBGVA-C3 A) |
| 8. (±)-Cannabichromene (CBC-C5) |
| 9. (+)-Cannabichromene acid ACBCA-C5 A |
| 10. (+)-Cannabivarichromene or (+)-Cannabichromevarin (CBCV-C3) |
| 11. (+)-Cannabichromevarinic acid A (CBCVA-C3 A) |
| 12. (−)-Cannabidiol (CBD-C5) |
| 13. Cannabidiol momomethyl ether (CBDM-C5) |
| 14. Cannabidiol-C4 (CBD-C4) |
| 15. (−)-Cannabidivarin CBDV-C3 |
| 16. Cannabidiorcol (CBD-C1) |
| 17. Cannabidiolic acid (CBDA-C5) |
| 18. Cannabidivarinic acid (CBDVA-C3) |
| 19. Cannabinodiol (CBND-C5) |
| 20. Cannabinodivarin (CBND-C3) |
| 21. Δ9-Tetrahydrocannabinol (Δ9-THC-C5) |
| 22. Δ9-Tetrahydrocannabinol-C4 (Δ9-THC-C4) |
| 23. Δ9-Tetrahydrocannabivarin (Δ9-THCV-C3) |
| 24. Δ9-Tetrahydrocannabiorcol (Δ9-THCO-C1) |
| 25. Δ9-Tetrahydro-cannabinolic acid A (Δ9-THCA-C5 A) |

| Cannabinoids isolated from *Cannabis* |
|---|
| 26. Δ9-Tetrahydro-cannabinolic acid B (Δ9-THCA-C5 B) |
| 27. Δ9-Tetrahydro-cannabinolic acid-C4A and/or B (Δ9-THCA-C4A and/or B) |
| 28. Δ9-Tetrahydro-cannabivarinic acid A (Δ9-THCVA-C3A) |
| 29. Δ9-Tetrahydro-cannabiorcolic acid A and/or B (Δ9-THCOA-C1A and/or B) |
| 30. (−)-Δ8-trans-(6aR,10aR)-Δ8-Tetrahydrocannabinol (Δ8-THC-C5) |
| 31. (−)-Δ8-trans-(6aR,10aR)-Tetrahydrocannabinolic acid A (Δ8-TFCA-C5 A) |
| 32. (−)-(6aS,10aR)-Δ9-Tetrahydrocannabinol ((−)-cis-Δ9-THC-C5) |
| 33. Cannabinol (CBN-C5) |
| 34. Cannabinol-C4 (CBN-C4) |
| 35. Cannabivarin (CBN-C3) |
| 36. Cannabivarin-C2 (CBN-C2) |
| 37. Cannabiorcol (CBN-C1) |
| 38. Cannabinolic acid A (CBNA-C5 A) |
| 39. Cannabinol methyl ether (CBNM-C5) |
| 40. (−)-(9R,10R)-trans-Cannabitriol ((−)-trans-CBT-C5) |
| 41. (+)-(9S,10S)-Cannabitriol ((+)-trans-CBT-C5) |
| 42. (±)-(9R,10S/9S,10R)-Cannabitriol ((±)-cis-CBT-C5) |
| 43. (−)-(9R,10R)-trans-10-O-Ethyl-cannabitriol ((−)-trans-CBT-OEt-C5) |
| 44. (±)-(9R,10R/9S,10S)-Cannabitriol-C3 ((±)-trans-CBT-C3) |
| 45. 8,9-Dihydroxy-Δ6a(10a)-tetrahydrocannabinol (8,9-Di-OH-CBT-C5) |
| 46. Cannabidiolic acid A cannabitriol ester (CBDA-C5 9-OH-CBT-C5 ester) |
| 47. (−)-(6aR,9S,10S,10aR)-9,10-Dihydroxy-hexahydrocannabinol, Cannabiripsol (Cannabiripsol-C5) |
| 48. (−)-6a,7,10a-Trihydroxy-Δ9-tetrahydrocannabinol ((−)-Cannabitetrol) |
| 49. 10-Oxo-Δ6a(10a)-tetrahydrocannabinol (OTHC) |
| 50. (5aS,6S,9R,9aR)-Cannabielsoin (CBE-C5) |
| 51. (5aS,6S,9R,9aR)-C3-Cannabielsoin (CBE-C3) |
| 52. (5aS,6S,9R,9aR)-Cannabielsoic acid A (CBEA-C5 A) |
| 53. (5aS,6S,9R,9aR)-Cannabielsoic acid B (CBEA-C5 B) |
| 54. (5aS,6S,9R,9aR)-C3-Cannabielsoic acid B (CBEA-C3 B) |
| 55. Cannabiglendol-C3 (OH-iso-HHCV-C3) |
| 56. Dehydrocannabifuran (DCBF-C5) |
| 57. Cannabifuran (CBF-C5) |
| 58. (−)-Δ7-trans-(1R,3R,6R)-Isotetrahydrocannabinol |
| 59. (±)-Δ7-1,2-cis-(1R,3R,6S/1S,3S,6R)-Isotetrahydro-cannabivarin |
| 60. (−)-Δ7-trans-(1R,3R,6R)-Isotetrahydrocannabivarin |
| 61. (±)-(1aS,3aR,8bR,8cR)-Cannabicyclol (CBL-C5) |
| 62. (±)-(1aS,3aR,8bR,8cR)-Cannabicyclolic acid A (CBLA-C5 A) |
| 63. (±)-(1aS,3aR,8bR,8cR)-Cannabicyclovarin (CBLV-C3) |
| 64. Cannabicitran (CBT-C5) |
| 65. Cannabichromanone (CBCN-C5) |
| 66. Cannabichromanone-C3 (CBCN-C3) |
| 67. Cannabicoumaronone (CBCON-C5) |
| 68. Cannabielsoin acid A (CBEA-A) |
| 69. 10-Ethoxy-9-hydroxy-delta-6a-tetrahydrocannabinol |
| 70. Cannabitriolvarin (CBTV) |
| 71. Delta-9-tetrahydrocannabiorcolic acid (THCA-C1) |
| 72. Delta-7-cis-iso-tetrahydrocanna |
| 73. Cannabichromanon (CBCF) |

| Structure of common cannaboinoids |
|---|

CBD

| Structure of common cannabinoids | Structure of common cannabinoids |
|---|---|
| 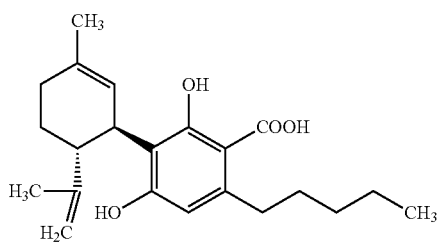<br>CBDA | 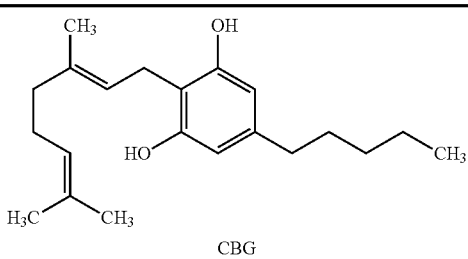<br>CBG |
| 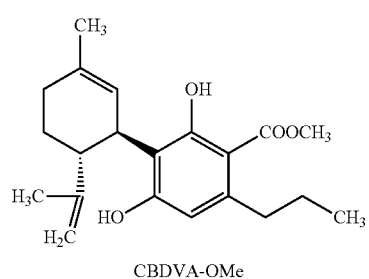<br>CBDVA-OMe | 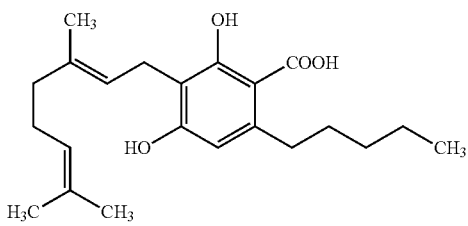<br>CBGA |
| 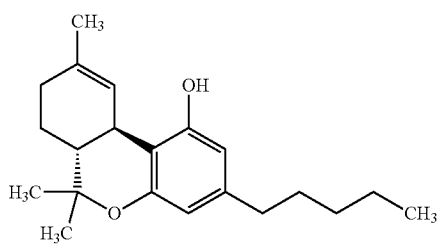<br>THC | 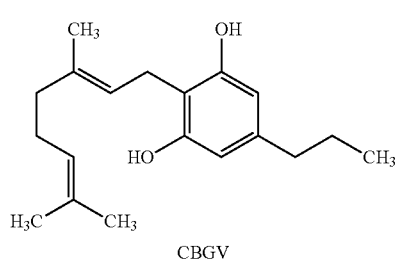<br>CBGV |
| 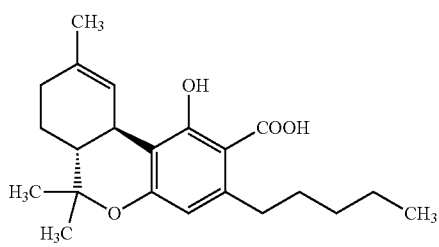<br>THCA | 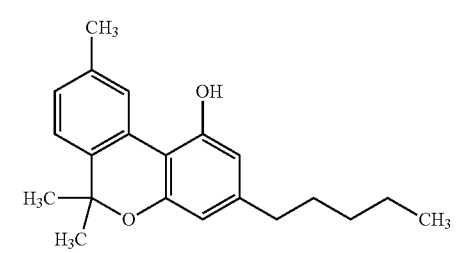<br>CBN |
| 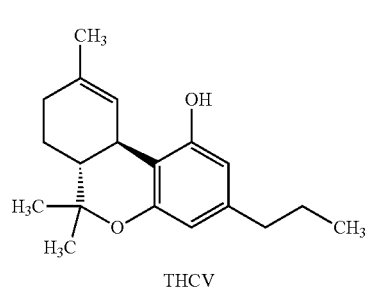<br>THCV | 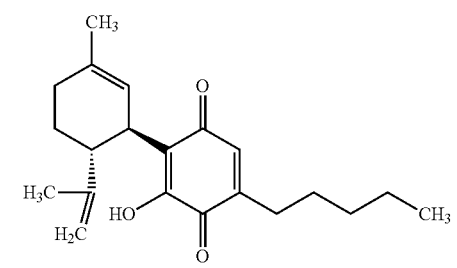<br>CBQ |
| | 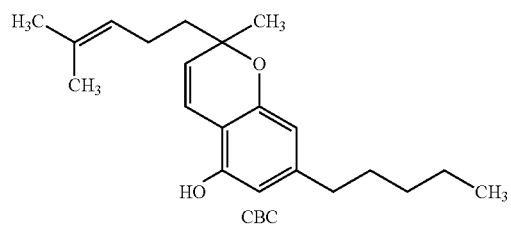<br>CBC |

Structure of common cannaboinoids

CBL

CBGB

CBGBA

CBDBA

CBDVA

THCVA

Synthetically prepared cannabinoids, that are commercially available (e.g., Purisys™ of Athens Ga.), are provided below.

| Common Name | Other Names | Alkyl Tail Length | CAS # |
|---|---|---|---|
| TETRAHYDROCANNABIVARIN FAMILY ||||
| Δ9-Tetrahydrocannabivarin | Δ9-THCV | C3 | 31262-37-0 |
| Δ8-Tetrahydrocannabivarin | Δ8-THCV | C3 | 31262-38-1 |
| Δ9-Tetrahydrocannabivarin Naphtoylester | Δ9-THCV-NE | C3 | N/A |
| Δ8-Tetrahydrocannabivarin Naphtoylester | Δ8-THCV-NE | C3 | N/A |
| Δ9-Tetrahydrocannabivarinic Acid | Δ9-THCVA-A, Δ9-THC-VA-B | C3 | 39986-26-0 |

| Common Name | Other Names | Alkyl Tail Length | CAS # |
|---|---|---|---|
| CANNABIDIOLVARIN FAMILY ||||
| (−)-Cannabidivarin | (−)-CBDV | C3 | 24274-48-4 |
| (+)-Cannabidivarin | (+)-CBDV | C3 | 1637328-94-9 |
| Cannabidivarinic Acid | CBDVA | C3 | 31932-13-S |
| Cannabidivarin Quinone | CBQV | C3 | N/A |
| TETRAHYDROCANNABIBUTOL FAMILY ||||
| Δ9-Tetrahydrocannabibutol | Δ9-THCB | C4 | 60008-00-6 |
| Δ8-Tetrahydrocannabibutol | Δ8-THCB | C4 | 51768-59-3 |
| Δ9-Tetrahydrocannabibutol Naphtoylester | Δ9-THCB-NE | C4 | 60007-98-9 |
| Δ8-Tetrahydrocannabibutol Naphtoylester | Δ8-THCB-NE | C4 | N/A |
| Δ9-Tetrahydrocannabibutolic Acid | Δ9-THCBA-A, Δ9-THC-BA-B | C4 | 60007-98-9 |

| Common Name | Other Names | Alkyl Tail Length | CAS # |
|---|---|---|---|
| CANNABIDIBUTOL FAMILY ||||
| (−)-Cannabidibutol | (−)-CBDB | C4 | 60113-11-3 |
| (+)-Cannabidibutol | (+)-CBDB | C4 | N/A |
| Cannabidibutolic Acid | CBDBA | C4 | N/A |

| Common Name | Other Names | Alkyl Tail Length | CAS # |
|---|---|---|---|
| RARE CANNABINOIDS ||||
| Cannabinol | CBN, USP Impurity | C5 | 521-35-7 |
| Cannabinolic Acid | CBNA | C5 | 2808-39-1 |
| Cannabigerol | CBG | C5 | 25654-31-3 |
| Cannabigerolic Acid | CBGA | C5 | 25555-57-1 |
| Cannabichromene | CBC | C5 | 20675-51-8 |
| Cannabichromenic Acid | CBCA | C5 | 185505-15-1 |
| Cannbicyclol | CBL | C5 | 21366-63-2 |
| Cannabicyclolic Acid | CBLA | C5 | 2283314-84-9 |
| Cannabivarin | CBNV | C3 | 33745-21-0 |
| Cannabivarinic Acid | CBNVA | C3 | 64846-02-2 |
| Cannbigerivarin | CBGV | C3 | 55824-11-8 |
| Cannabigerivarinic Acid | CBGVA | C3 | 64924-07-8 |
| Cannbichromevarin | CBCV | C3 | 57130-04-8 |

-continued

| Common Name | Other Names | Alkyl Tail Length | CAS # |
|---|---|---|---|
| Cannabichromevarinic Acid | CBCVA | C3 | 64898-02-8 |
| Cannabicyclolvarin | CBLV | C3 | 55870-47-8 |
| Cannabicyclolvarinic Acid | CBLVA | C3 | 2281847-63-8 |
| 3-Butylcannabinol | CBNB | C4 | 60007-99-0 |
| 3-Butylcannabinolic Acid | CBNBA | C4 | N/A |
| Cannabigerol Butyl | CBGB | C4 | N/A |
| Cannabigerol Butyric Acid | CBGBA | C4 | N/A |
| Cannabichromene Butyl | CBCB | C4 | N/A |
| Cannabichromene Buytric Acid | CBCBA | C4 | N/A |
| Cannabicyclol Butyl | CBLB | C4 | N/A |
| Cannabicyclol Butyric Acid | CBLBA | C4 | N/A |

The term "terpene" refers to a hydrocarbon or derivative thereof, found as a natural product and biosynthesized by oligomerizaion of isoprene units. A terpene can be a cyclic, monocyclic, bicyclic, or multicyclic. Examples include, e.g., sesquiterpenes (e.g., (−)-β-caryophyllene, humulene, vetivazulene, guaiazulene, longifolene, copaene, and patchoulol), monoterpenes (e.g., limonene and pulegone), monoterpenoids (e.g., carvone), diterpenes (e.g., taxadiene), and triterpenes (e.g., squalene, betulin, betulinic acid, lupane, lupeol, betulin-3-caffeate, allobetulin, and cholesterol). The terpene can be synthetically prepared, or alternatively, can be obtained naturally (e.g., from plant matter). Either way, the terpene can have the requisite purity (e.g., at least 95 wt % pure, at least 98 wt. % pure, at least 99 wt % pure, or at least 99.5 wt % puree).

| Terpene | Plant | Genus | Species |
|---|---|---|---|
| Myrcene | Myrtles | *Myrtus* | *communis; nivellei; phyllireaefolia* |
| | Cannabis | *Cannabis* | *sativa; ruderalis; indica* |
| Linalool | Mint | *Mentha* | *spicata; arvensis; canadensis* |
| | Lavender | *Lavandula* (subgenus: *Fabricia; Sabaudia*) | *spica; angustifolia; latifolia; lanata; dentata; stoechas; pedunculata; viridis* |
| Terpineol | Orange peel | *Citrus* | *reticulata* |
| | Junipers | *Juniperus* | *communis; chinensis; conferta; rigida* |
| Camphene | Chrysanthemum | *Chrysanthemum* | *indicum* |
| | Ginger | *Zingiber* | *officinale* |
| Bisabolol | Chamomile | *Matricaria* (or *Chamaemelum*) | *chamomilla* (or *nobile*) |
| | Figwort | *Myoporum* | *crassifolium* |
| Nerolidol | Cannabis | *Cannabis* | *sativa; ruderalis; indica* |
| Limonene | Citrus Lemon | *Citrus* | *limon* |
| Humulene | Hops | *Humulus* | *lupulus; japonicus; yunnanensis* |
| Terpinolene | Cannabis | *Cannabis* | *sativa; ruderalis; indica* |
| Carene | Rosemary | *Salvia* | *rosmarinus; jordanii* |
| | Cedar | *Cedrus* | *atlantica; brevifolia; deodara; libani* |
| Eucalyptol | Eucalyptus | *Eucalyptus* | *obliqua* |
| | Cannabis | *Cannabis* | *sativa; ruderalis; indica* |
| | Camphor laurel | *Cinnamomum* | *camphora* |
| | Bay leaves | *Laurus* | *nobilis* |
| | Wormwood | *Artemisia* | *vulgaris* |
| Ocimene | Hops | *Humulus* | *lupulus; japonicus; yunnanensis* |
| | Kumquats | *Citrus* | *japonica* |
| | Mango | *Mangifera* | *indica* |
| | Basil | *Ocimum* | *basilicum* |
| | bergamot orange | *Citrus* | *x aurantium* |
| Carophyllene | Peppercorn | *Piper* | *nigrum* |
| | Cloves | *Syzgium* | *aromaticum* |
| | Cannabis | *Cannabis* | *sativa; ruderalis; indica* |
| | Rosemary | *Salvia* | *rosmarinus; jordanii* |
| | Hops | *Humulus* | *lupulus; japonicus; yunnanensis* |
| Valencene | Nootka cypress | *Callitropsis* | *nootkatensis* |
| Geraniol | Roses | *Rosa* (subgenus: *Banksianae, Bracteatae, Caninae, Carolinae, Chinensis, Gallicanae, Gymnocarpae, Laevigatae, Pimpinellifoliae, Synstylae*) | *persica; minutifolia; stellata* |
| | Wine grapes | *Vitis* | *vinifera* |
| Borneol | Borneo camphor | *Dryobalanops* | *aromatica* |
| | Ngai camphor; sambong | *Blumea* | *balsamifera* |
| Pulegone | Catnip | *Nepeta* | *cataria* |
| | Peppermint | *Mentha* | *piperita* |
| | Pennyroyal | *Hedeoma* | *pulegioides* |

| Terpene | Plant | Genus | Species |
|---|---|---|---|
| Guaiazulene | Chamomile | *Matricaria* (or *Chamaemelum*) | *chamomilla* (or *nobile*) |
| | Guaiacum tree | *Guaiacum* | *sanctum, angustifolium, coulteri, officinale* |
| Lupeol | Lupine seed | *Lupinus* | *luteus* |
| Lupane | Lupine seed | *Lupinus* | *luteus* |
| Betulin Betulinic acid Lupeol | Brich tree | *Betula* (Subgenus: *Betulenta, Betulaster, Neurobetula, Chamaebetula*) | *alleghaniensis, cordifolia, glandulosa, lenta, michauxii, minor, nana, neoalaskana, nigra, occidentalis, papyrifera, populifolia, pumila, uber* |
| Squalene | Amaranth seed | *Amaranthus* (subgenus: *Acnida; Albersia*) | *acanthochiton, acutilobus, albus, anderssonii, californicus* |
| | Wheat germ | *Triticum* | *aestivum* |
| | Olive | *Olea* | *europaea* |
| Carvone | Caraway seed | *Carum* | *carvi* |
| | Spearmint | *Mentha* | *spicata* |
| | Dill | *Anethum* | *graveolens* |
| Patchoulol | Patchouli | *Pogostemon* | *cablin* |
| Copaene | Copaiba tree | *Copaifera* | *langsdorfii* |
| Longifolene | Pine | *Pinus* | *longifolia* |
| Pinene | Pine | *Pinus* (subgenus: *Strobus; Pinus*) | *densata, densiflora, pinea, sylvestris* |
| Vetivazulene | Vetiver | *Chrysopogon* | *zizanioides* |
| Nerol | Lemon Grass | *Cymbopogon* | *nardus; citratus; flexuosus; martinii; schoenanthus* |

Synthetically prepared terpenes, which are commercially available (e.g., Purisys™ of Athens Ga.), are provided below.

| Terpene | CAS # |
|---|---|
| Alpha-Pinene | 51634232009 |
| Beta-Pinene | 51634232109 |
| Beta-Myrcene | 51634232209 |
| Alpha-Terpinene | 51634232309 |
| Limonene | 51634232409 |
| Beta-Ocimene | 51634232509 |
| Terpinolene | 51634232609 |
| Linalool | 51634232709 |
| Fenchyl Alcohol | 51634232809 |
| Borneol Isomers | 51634232909 |
| Alpha-Terpineol | 51634233009 |
| Trans-caryophyllene | 51634233109 |
| Alpha-humulene | 51634233209 |
| Trans-nerolidol | 51634233309 |
| Guaiol | 51634233409 |
| Alpha-Bisabolol | 51634233509 |

The term "flavonoid" refers to ubiquitous plant natural products with various polyphenolic structures. Flavonoids can be extracted from fruits, vegetables, grains, bark, roots, stems, flowers, and teas or can be biosynthetically produced. The role of flavonoids in plants includes UV protection, aid in plant growth, defense against plaques, and provide the color and aroma of flowers.

Flavonoids can be divided into classes (e.g., anthocyanin, chalcone, flavone, flavonol, isoflavone, and flavonone) and subclasses depending on the carbon of the C ring on which the B ring is attached and the degree of unsaturation and oxidation of the C ring.

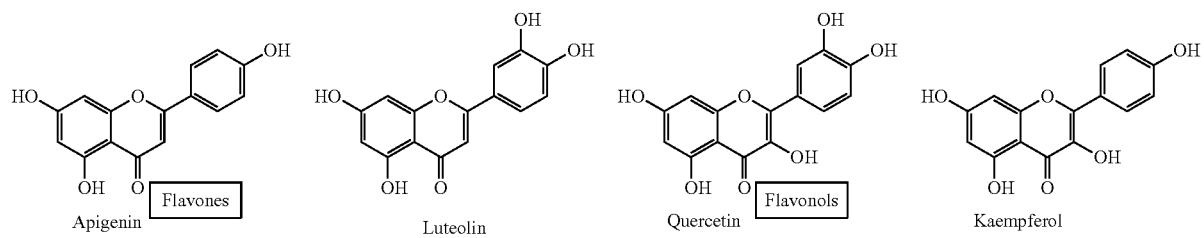

-continued

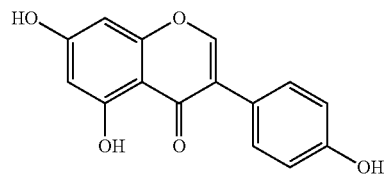

Genistein

[Isoflavones]

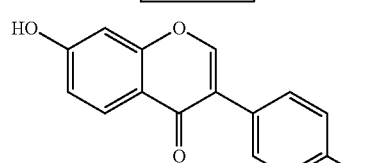

Daidzein

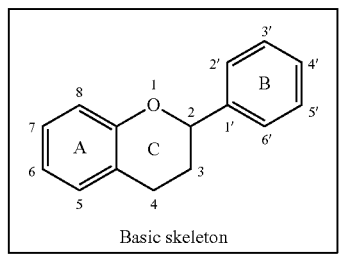

Basic skeleton

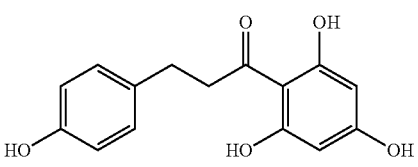

Phloretin

[Chalcones]

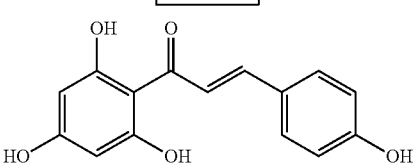

Chalconaringenin

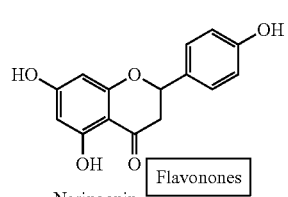

Naringenin [Flavonones]

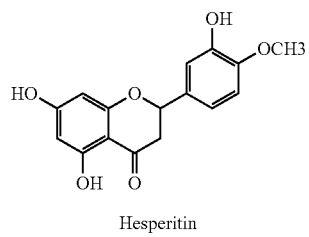

Hesperitin

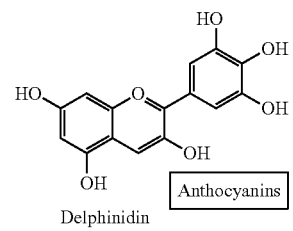

Delphinidin [Anthocyanins]

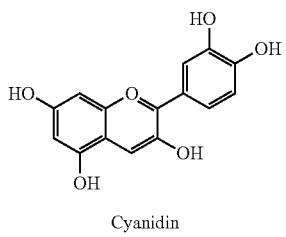

Cyanidin

| Flavonoid classes | Subclasses | Natural sources | Examples of natural sources |
|---|---|---|---|
| Anthocyanins | Cyanidin, Malvidin, Delphinidin, Peonidin | Fruits, vegetables, nuts, dried fruits, medicinal plants | Cranberries, plums, cherries, sweet potatoes, black currants, red grapes, merlot grapes, raspberries, strawberries, blueberries, bilberries and blackberries |
| Chalcones | Phloretin, Arbutin, Phloridzin | Fruits, vegetables, medicinal plants | Tomatoes, pears, strawberries, bearberries and certain wheat products |
| Flavonones | Hesperitin, Naringin, Naringenin, Eriodictyol, Hesperidin | Fruits (citrus), medicinal plants | Oranges, lemons, grapes, rosehips |
| Flavones | Apigenin, Tangeretin, Baicalein, Rpoifolin | Fruits, medicinal plants | Celery, parsley, red peppers, chamomile, mint, ginkgo biloba, broccoli, green pepper, thyme, dandelion, perilla, tea, carrot, rosemary, oregano, Cannabis sativa |
| Flavonols | Quercetin, Myricetin, Rutin, Morin, Kaempferol | Fruits, vegetables, medicine plants | Onion, kale, lettuce, tomatoes, apples, grapes, berries, tea, red wine, broccoli, potatoes, brussel sprouts, squash, cucumbers, lettuce, green beans, spinach, peaches, blackberries |

| Flavonoid classes | Subclasses | Natural sources | Examples of natural sources |
|---|---|---|---|
| Isoflavonoids | Genistin, Genistein, Daidzein, Glycetein, Daidzin | Legumes, medicinal plants | Soybeans, lupin, fava beans, kudzu, psoralea, red clover, alfalfa sprouts, peanuts, chickpeas |

| Flavonoid classes | Structure of flavonoid classes |
|---|---|
| Anthocyanins | Double bonds between positions 1 and 2, 3 and 4 of the C ring; Hydroxyl groups at positions 5 and 7 in the A ring and 3', 4' and/or 5' of the B ring; Methylation or acylation at the hydroxyl groups on the A and B rings vary |
| Chalcones | Absence of 'C ring' of the basic flavonoid skeleton |
| Flavonones | structure C ring is saturated (contains no double bonds) |
| Flavones | Double bond between positions 2 and 3 and a ketone in position 4 of the C ring; Most have a hydroxyl group in position 5 or 7 of the A ring of the A ring or 3' and 4' of the B ring (varies according to the taxonomic classification of the particular plant) |
| Flavonols | Double bond between positions 2 and 3, a ketone in position 4 and hydroxyl group in position 3 of the C ring; the ketone group the C ring may also be glycosylated; very diverse in methylation and hydroxylation patterns |
| Isoflavonoids | B ring is attached to the 3 position of the C ring and contains a hydroxyl group at the 4' position; hydroxylation of the A ring varies |

Studies on flavonoids have revealed an increasing number of health benefits showing anti-oxidant, anti-inflammatory, anti-mutagenic, and anti-carcinogenic properties by inhibiting numerous pro-inflammatory and pro-oxidative enzymes (e.g., xanthine oxidase (XO), cyclo-oxygenase (COS), lipoxygenase, phosphoinositide 3-kinase, and acetylcholinesterase). This may have benefits towards numerous diseases and medical conditions (e.g., pain, cancer, artherosclerosis, Alzheimer's disease). There is a growing interest in the medicinal properties of Cannabis (Cannabis sativa, Cannabis indica, Cannabis ruderalis). Studies have shown that Cannaflavin A and Cannflavin B, prenylated flavones, have anti-inflammatory properties greater than aspirin. Cannflavin A and B can be isolated from Cannabis sativa and biosynthesized.

Synthetically prepared flavonoids, which are commercially available (e.g., Cannflavin B from Toronto Research Chemicals), are provided below.

| Flavonoid | CAS # |
|---|---|
| Cannflavin A | 76735-57-4 |
| Cannflavin B | 76735-58-5 |
| Myricetin | 529-44-2 |
| (−)-Epigallocatechin gallate | 989-51-5 |
| Polyphenon 60 from green tea | 138988-88-2 |
| (−)-Gallocatechin | 3371-27-5 |
| Kaempferol | 520-18-3 |
| (±)-Catechin hydrate | 7295-85-4 (anhydrous) |
| Galangin | 548-83-4 |
| Hesperidin | 520-26-3 |
| Baicalein | 491-67-8 |
| Icariin | 489-32-7 |
| Orientin | 28608-75-5 |
| Liquiritigenin | 578-86-9 |
| Acacetin | 480-44-4 |
| Diosmetin | 520-34-3 |
| Scutellarein | 529-53-3 |
| Luteolin | 491-70-3 |

The flavonoid can be synthetically prepared, or alternatively, can be obtained naturally (e.g., from plant matter). Either way, the flavonoid can have the requisite purity (e.g., at least 95 wt. % pure at least 98 wt % pure, at least 99 wt % pure, or at least 99.5 wt % pure).

The term "transdermal delivery agent" refers to a substance that aids or facilitates the passage of desired compounds, such as pharmaceutically active ingredients (e.g., external analgesic agent), cannabinoids, and/or terpenes, at least partially or fully through one or more layers of the skin, including the dermis and epidermis. The topical analgesic compositions described herein can optionally include one or more transdermal delivery agents.

The term "antioxidant" refers to an oxidation preventive agent that reduces excessive production of reactive oxygen species. Antioxidants can come from natural products or sources such as vitamin E (tocopherol), vitamin C (ascorbic acid), vitamin A, β-carotene, superoxide dismutase, coenzyme Q. Synthetically derived antioxidants include 3,5-tert-butyl-4-hydroxytoluene (BHT) and 2,3-tert-butyl-hydroxyanisole (BHA) which have been developed to inhibit oxidation of a lipid or the like. The topical analgesic compositions described herein can optionally include one or more antioxidants.

The term "microcirculation stimulant" refers to a compound that enhances the circulation of the blood in the microvessels, the smallest blood vessels, of the microvasculature present within organ tissues, such as the muscle. The microvessels include terminal arterioles, metarterioles, capillaries, and venules. Examples of microcirculation stimulants include caffeine, theophylline, theobromine and L-theanine. The topical analgesic compositions described herein can optionally include one or more microcirculation stimulants.

The term "preservative" refers to a compound or chemical added to slow or prevent decay of a product (ie, topical cream, cosmetics, foods, wood, etc.). Examples of preservatives include butylparaben, ethylparaben, methylparaben, propylparaben, sorbic acid, benzyl alcohol, salicylic acid, formaldehyde, tetrasodium ethylenediaminetetra-acetic acid (EDTA), neroli hydrosol, phenoxyethanol, ethylhexylglycerin, methylisothiazolinone, methylchloroisothiazolinone, citric acid, sodium benzoate, and tetrasodium glutamate diacetate. The topical analgesic compositions described herein can optionally include one or more preservatives.

The term "herbal active ingredient" refers to a biologically active compound used in a pharmaceutical drug that was extracted from a plant. An example of an herbal active ingredient is salicin, which can be extracted from white willow bark extract that is used as a natural topical pain remedy. The topical analgesic compositions described herein can optionally include one or more herbal active ingredients.

The term "pH adjusting agent" refers to a buffering agent that is an acid or base used to maintain the acidity of a solution at a chosen value. Examples of pH adjust agents include sodium bicarbonate, triethanolamine, citric acid, sodium gluconate, magnesium hydroxide, and lactic acid. The topical analgesic compositions described herein can optionally include one or more pH adjusting agents.

The term "fragrance" refers to a combination of chemicals that gives each product its distinct scent. Chemical ingredients may be derived from synthetic or natural raw materials that can add or mask a scent. The ingredients are capable of imparting or modifying the odor of skin or hair or other substrate. The topical analgesic compositions described herein can optionally include one or more fragrances.

The term "coloring agent" refers to a natural or synthetic compound that provides a pigment used to enhance the product's appearance and aesthetic value. The topical analgesic compositions described herein can optionally include one or more coloring agents.

The term "skin surface" refers to interface of an organism with the environment, which prevents moisture loss from the body, and is a barrier functioning to prevent the invasion of biotoxic substances, such as microorganisms and allergens, from the environment. The skin contains two layers consisting of an outer epidermis and an inner dermis.

The term "human" refers to a person who can benefit from the pharmaceutical formulations and methods of the present invention. The person that could benefit from the presently described pharmaceutical formulations and methods may be an adolescent or adult. A human may be referred to as an individual, patient, subject, or recipient.

The term "subject" is used herein to generally include humans, particularly human adolescents (e.g., 12-17 years old) and human adults (e.g., at least 18 years old).

The term "topical formulation" is used herein to generally include a formulation that can be applied to a skin surface. Topical formulations may, for example, be used to confer therapeutic benefit to a patient or pain relief to a consumer. Topical formulations can be used for both topical and transdermal administration of substances. The topical formulations can be configured and formulated to exist in various dosage forms, such as, e.g., gel, pump gel, gel packet, cream, lotion, roll-on liquid, roll-on gel, spray, pump spray, aerosol spray, stick, patch, ointment, liniment, or balm.

The term "topical administration" is used herein to generally include the delivery of a substance, such as a therapeutically active agent (e.g., external analgesic agent), to the skin or a localized region of the body.

The term "transdermal administration" is used herein to generally include administration through at least a portion of the skin. Transdermal administration is often applied for delivering desired substances to tissues underlying the skin with minimal or partial systemic absorption. As such, the transdermal administration delivers desired substances at least partially through one or more layers of the skin, including the dermis and epidermis.

The term "effective amount" is used herein to generally include an amount of topical formulation (or external analgesic agent) effective for treating muscle pain or aches in a subject as described herein.

The term "treating" with regard to a subject, refers to improving at least one symptom of the subjects disorder. Treating includes curing, improving, or at least partially ameliorating the disorder or the symptoms thereof.

Method of Manufacturing

As described herein, the compositions of the present invention are suitable for topical (e.g., dermal or intradermal) administration and include, e.g., liquid or semi-solid preparations (e.g., liniments, lotions, gels, sprays, foams, film forming systems, microneedles, micro- or nano-emulsions), and oil-in-water or water-in-oil emulsions (e.g., creams, ointments or pastes). These topical dosage forms can be prepared employing well-known and routine procedures, equipment, techniques, and substances. See, e.g., A. Williams, Transdermal and Topical Delivery Systems, Pharmaceutical Press, London and Chicago, 2003; L. Lachman, The Theory and Practice of Industrial Pharmacy, 4th Ed., Stipes Publishing, 2015; Remington, Pharmaceutical Sciences, $22^{nd}$ Rev., Pharmaceutical Press, 2012; H. Benson, Topical and Transdermal Drug Delivery: Principles and Practice 1st Edition, Wiley, 2012; D. Osborne, Topical Drug Delivery Formulations (Drugs and the Pharmaceutical Sciences) 1st Edition, CRC Press, 1989; and M. Brown, The Art and Science of Dermal Formulation Development (Drugs and the Pharmaceutical Sciences) 1st Edition, CRC Press, 2019.

Specific Ranges, Values, and Embodiments

The specific embodiments describing the ranges and values provided below are for illustration purposes only, and do not otherwise limit the scope of the disclosed subject matter, as defined by the claims.

In specific embodiments, the topical analgesic includes at least one of a cannabinoid, terpene, and flavonoid.

In specific embodiments, the topical analgesic includes a cannabinoid obtained as a distillate from *cannabis*.

In specific embodiments, the topical analgesic includes a cannabinoid obtained as an extract from *cannabis*.

In specific embodiments, the topical analgesic includes a cannabinoid obtained as a supercritical fluid extract from *cannabis*.

In specific embodiments, the topical analgesic includes a cannabinoid obtained as a supercritical fluid extract from *cannabis*, utilizing carbon dioxide ($CO_2$) as the supercritical fluid solvent.

In specific embodiments, the topical analgesic includes a cannabinoid obtained as a resin from *cannabis*.

In specific embodiments, the topical analgesic includes a cannabinoid isolate obtained from *cannabis*.

In specific embodiments, the topical analgesic includes a cannabinoid present as an oil from *cannabis*.

In specific embodiments, the topical analgesic includes a cannabinoid present as hempseed oil.

In specific embodiments, the topical analgesic includes a cannabinoid that is synthetically prepared.

In specific embodiments, the topical analgesic includes a cannabinoid that is at least one of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

In specific embodiments, the topical analgesic includes a cannabinoid that is at least one of CBD and THC.

In specific embodiments, the topical analgesic includes a terpene.

In specific embodiments, the topical analgesic includes a sesquiterpene.

In specific embodiments, the topical analgesic includes a terpene obtained as a distillate from plant matter.

In specific embodiments, the topical analgesic includes a terpene obtained as an extract from plant matter.

In specific embodiments, the topical analgesic includes a terpene obtained from *Cannabis sativa, Syzygium aromaticum* (cloves), rosemary, or hops.

In specific embodiments, the topical analgesic includes a terpene that is synthetically prepared.

In specific embodiments, the topical analgesic includes a terpene that is Beta-Caryophyllene.

In specific embodiments, the topical analgesic includes a flavonoid.

In specific embodiments, the topical analgesic includes a flavone.

In specific embodiments, the topical analgesic includes an isoflavone.

In specific embodiments, the topical analgesic includes a cannflavin.

In specific embodiments, the topical analgesic includes a flavonoid which is at least one of an anthocyanin (e.g., cyanidin, malvidin, delphinidin, or peonidin), chalcone (e.g., phloretin, arbutin, or phlioridzin), flavonone (e.g., hesperitin, naringin, naringenin, eriodictyol, or hesperidin), flavone (e.g., apigenin, tangeretin, baicalein, or rpoifolin), flavonol (e.g., quercetin, myricetin, rutin, morin, or kaempferol), and isolavonoid (e.g., genistin, genistein, daidzein, glycetein, or daidzin).

In specific embodiments, the topical analgesic includes a flavonoid which is at least one of Cannflavin A, Cannflavin B, Myricetin, (−)-Epigallocathechin gallate, Polyphenon 60 from green tea, (−)-Gallocathechin, Kaempferol, (+)-Catechin hydrate, Galangin, Hesperidin, Baicalein, Icariin, Orientin, Liquiritigenin, Acacetin, Diosmetin, Scutellarein, and Luteolin.

In specific embodiments, the topical analgesic includes at least one of a cannabinoid, terpene, and flavonoid, present in an aggregate amount of up to 20 wt. %.

In specific embodiments, the topical analgesic includes at least one of a cannabinoid, terpene, and flavonoid, present in an aggregate amount of up to 15 wt. %.

In specific embodiments, the topical analgesic includes at least one of a cannabinoid, terpene, and flavonoid, present in an aggregate amount of up to 10 wt. %.

In specific embodiments, the topical analgesic includes at least one of a cannabinoid, terpene, and flavonoid, present in an aggregate amount of up to 5 wt. %.

In specific embodiments, the topical analgesic includes at least one of a cannabinoid, terpene, and flavonoid, present in an aggregate amount of up to 2.5 wt. %.

In specific embodiments, the topical analgesic includes at least one of a cannabinoid, terpene, and flavonoid, present in an aggregate amount of up to 1 wt. %.

In specific embodiments, the topical analgesic includes at least one of a cannabinoid, terpene, and flavonoid, present in an aggregate amount of up to 0.75 wt. %.

In specific embodiments, the topical analgesic includes at least one of a cannabinoid, terpene, and flavonoid, present in an aggregate amount of up to 0.5 wt. %.

In specific embodiments, the topical analgesic includes at least one of a cannabinoid, terpene, and flavonoid, present in an aggregate amount of at least 0.01 wt. %.

In specific embodiments, the topical analgesic includes at least one of a cannabinoid, terpene, and flavonoid, present in an aggregate amount of at least 0.05 wt. %.

In specific embodiments, the topical analgesic includes at least one of a cannabinoid, terpene, and flavonoid, present in an aggregate amount of at least 0.1 wt. %.

In specific embodiments, the topical analgesic includes at least one of a cannabinoid, terpene, and flavonoid, present in an aggregate amount of at least 0.15 wt. %.

In specific embodiments, the topical analgesic includes at least one of a cannabinoid, terpene, and flavonoid, present in an aggregate amount of at least 0.20 wt. %.

In specific embodiments, the topical analgesic includes at least one of a cannabinoid, terpene, and flavonoid, present in an aggregate amount of at least 0.25 wt %.

In specific embodiments, the topical analgesic includes at least one of a cannabinoid, terpene, and flavonoid, present in an aggregate amount of at least 0.30 wt. %.

In specific embodiments, the topical analgesic includes at least one of a cannabinoid, terpene, and flavonoid, present in an aggregate amount of at least 0.35 wt. %.

In specific embodiments, the topical analgesic includes at least one of a cannabinoid, terpene, and flavonoid, present in an aggregate amount of at least 0.40 wt. %.

In specific embodiments, the topical analgesic includes at least one of a cannabinoid, terpene, and flavonoid, present in an aggregate amount of at least 0.45 wt. %.

In specific embodiments, the topical analgesic includes at least one of a cannabinoid, terpene, and flavonoid, present in an aggregate amount of at least 0.50 wt. %.

In specific embodiments, the topical analgesic includes at least one of a cannabinoid, terpene, and flavonoid, present in an aggregate amount of 0.01-2.0 wt. %.

In specific embodiments, the topical analgesic includes at least one of a cannabinoid, terpene, and flavonoid, present in an aggregate amount of 0.01-1.0 wt. %.

In specific embodiments, the topical analgesic includes at least one of a cannabinoid, terpene, and flavonoid, present in an aggregate amount of 0.01-0.75 wt. %.

In specific embodiments, the topical analgesic includes at least one of a cannabinoid, terpene, and flavonoid, present in an aggregate amount of 0.01-0.5 wt. %.

In specific embodiments, the topical analgesic includes at least one of a cannabinoid, terpene, and flavonoid, present in an aggregate amount of 0.05-2.0 wt. %.

In specific embodiments, the topical analgesic includes at least one of a cannabinoid, terpene, and flavonoid, present in an aggregate amount of 0.05-1.0 wt. %.

In specific embodiments, the topical analgesic includes at least one of a cannabinoid, terpene, and flavonoid, present in an aggregate amount of 0.05-0.75 wt. %.

In specific embodiments, the topical analgesic includes at least one of a cannabinoid, terpene, and flavonoid, present in an aggregate amount of 0.05-0.5 wt %.

In specific embodiments, the topical analgesic includes at least one of a cannabinoid, terpene, and flavonoid, present in an aggregate amount of 0.1-2.0 wt. %.

In specific embodiments, the topical analgesic includes at least one of a cannabinoid, terpene, and flavonoid, present in an aggregate amount of 0.1-1.0 wt. %.

In specific embodiments, the topical analgesic includes at least one of a cannabinoid, terpene, and flavonoid, present in an aggregate amount of 0.1-0.75 wt. %.

In specific embodiments, the topical analgesic includes at least one of a cannabinoid, terpene, and flavonoid, present in an aggregate amount of 0.1-0.5 wt. %.

In specific embodiments, the topical analgesic includes at least one of a cannabinoid, terpene, and flavonoid, present in an aggregate amount of 0.25-2.5 wt. %.

In specific embodiments, the topical analgesic includes at least one of a cannabinoid, terpene, and flavonoid, present in an aggregate amount of 0.25-1.5 wt. %.

In specific embodiments, the topical analgesic includes at least one of a cannabinoid, terpene, and flavonoid, present in an aggregate amount of 0.25-1.0 wt. %.

In specific embodiments, the topical analgesic includes at least one of a cannabinoid, terpene, and flavonoid, present in an aggregate amount of 0.25-0.75 wt. %.

In specific embodiments, the topical analgesic is in the form of a gel, pump gel, gel packet, cream, lotion, roll-on liquid, roll-on gel, spray, pump spray, aerosol spray, stick, patch, ointment, liniment, or balm.

In specific embodiments, the topical analgesic is in the form of a cram.

In specific embodiments, the topical analgesic includes at least one of a cannabinoid, terpene, and flavonoid; wherein the cannabinoid, terpene, flavonoid, or combination thereof, while present in the aggregate amounts, are characterized as an inactive ingredient.

In specific embodiments, the topical analgesic includes at least one of a cannabinoid, terpene, and flavonoid; wherein the cannabinoid, terpene, flavonoid, or combination thereof, while present in the aggregate amounts, are characterized as an active ingredient.

In specific embodiments, the topical analgesic includes at least one of a cannabinoid, terpene, and flavonoid; wherein the cannabinoid, terpene, flavonoid, or combination thereof, while present in the aggregate amounts, are characterized as an excipient.

In specific embodiments, the topical analgesic includes at least one of a cannabinoid, terpene, and flavonoid; wherein the cannabinoid, terpene, flavonoid, or combination thereof, while present in the aggregate amounts, are characterized as an analgesic.

In specific embodiments, the topical analgesic includes solvent, external analgesic, emulsifier, polymeric binder, solubility oil, cannabinoid, anti-oxidant, and preservative.

In specific embodiments, the solvent includes at least one of water, glycerin, propylene glycol, propanediol, butylene glycol, ethoxydiglycol, isododecane, isobexadecane, octyldodecanol, hexylene glycol, 1,2-hexanediol, and dicaprylyl carbonate.

In specific embodiments, the topical analgesic includes the solvent water.

In specific embodiments, the topical analgesic includes the solvent present in 88±5 wt. %.

In specific embodiments, the topical analgesic includes the solvent water, present in 88±5 wt. %.

In specific embodiments, the topical analgesic includes the external analgesic menthol.

In specific embodiments, the topical analgesic includes the external analgesic in 2.5±0.5 wt. %.

In specific embodiments, the topical analgesic includes at least one of: menthol, trolamine salicylate, camphor, capsaicin, lidocaine HCl, lidocaine, and methyl salicylate.

In specific embodiments, the topical analgesic includes at least one of: 0.75-16 wt. % menthol, 10±2 wt. % trolamine salicylate, 2-11 wt. % camphor, 0.025-0.15 wt. % capsaicin, 4±0.8 wt. % lidocaine HCl, 4±0.8 wt. % lidocaine, and 10-30 wt. % methyl salicylate.

In specific embodiments, the topical analgesic includes the external analgesic:
2-16 wt. % menthol,
10±2 wt. % trolamine salicylate,
3.1±0.7 wt. % camphor,
0.025-0.15 wt. % capsaicin,
4±0.8 wt. % lidocaine HCl,
4±0.8 wt. % lidocaine,
4-11 wt. % camphor and 8-16 wt. % menthol.
0.025 wt. % capsaicin and 10±2 wt. % menthol,
3-10 wt. % menthol and 15-30 wt. % methyl salicylate
4±0.8 wt. % lidocaine HCl and 1±0.25 wt. % menthol, or
3-7 wt. % camphor, 5-16 wt. % menthol, and 10-30 wt. % methyl salicylate.

In specific embodiments, the topical analgesic includes
2 wt. % menthol,
2.5 wt. % menthol,
4 wt. % menthol,
5 wt. % menthol,
7 wt. % menthol,
7.5 wt. % menthol,
10 wt. % menthol,
10.5 wt. % menthol,
16 wt. % menthol,
10% trolamine salicylate,
3.1 wt. % camphor,
0.025 wt. % capsaicin,
0.035 wt. % capsaicin,
0.1 wt % capsaicin,
0.15 wt % capsaicin,
4 wt. % lidocaine HCl,
4 wt. % lidocaine,
11 wt. % camphor and 16 wt. % menthol,
4 wt. % camphor and 16 wt. % menthol,
11 wt. % camphor and 11 wt. % menthol,
11 wt. % camphor and 10 wt. % menthol,
11 wt. % camphor and 8 wt. % menthol,
0.025 wt. % capsaicin and 10 wt % menthol,
10 wt. % menthol and 15 wt % methyl salicylate,
10 wt % menthol and 30 wt. % methyl salicylate
7.6 wt. % menthol, and 29 wt. % methyl salicylate
8 wt. % menthol and 16 wt. % methyl salicylate,
16 wt. % menthol and 28 wt. % methyl salicylate,
3 wt. % menthol and 10 wt. % methyl salicylate,
4 wt. % lidocaine HCl and 1 wt % menthol,
4 wt. % camphor, 10 wt. % menthol, and 30 wt. % methyl salicylate.
3 wt. % camphor, 5 wt. % menthol, and 15 wt % methyl salicylate,
7 wt % camphor, 16 wt. % menthol, and 25 wt. % methyl salicylate, or
3.1 wt. % camphor, 16 wt. % menthol, and 10 wt. % methyl salicylate.

In specific embodiments, the topical analgesic includes an emulsifier.

In specific embodiments, the topical analgesic includes the emulsifier polysorbate 60, laureth-4, potassium cetyl sulfate, cetyl alcohol, cetearyl alcohol, stearyl alcohol, glyceryl stearate, propylene glycol, polyglyceryl-6 laurate, ceteareth-20, PEG-100 stearate, sodium lauroyl lactylate, myristyl myristate, carbomer, polysorbate 80, polawax, sorbitan stearate, gum Arabic, *brassica* alcohol, cabomer 980 QD, sodium stearate, polyhydroxystearic acid, PEG-150 distearate, glyceryl oleate, emulsifying wax, glyceryl monooleate, phospholipids, polyoxyethylene alkyl ethers, polyoxyethylene, castor oil derivatives, sorbitan fatty acid esters, polyoxyethylene steartes, polyoxylglycerides, polysorbate, sorbitan esters, lecithin, or any combination thereof.

In specific embodiments, the topical analgesic includes an emulsifier present in 2±0.4 wt. %.

In specific embodiments, the topical analgesic includes the emulsifier lecithin.

In specific embodiments, the topical analgesic includes the emulsifier lecithin, wherein the lecithin is hydroxylated lecithin.

In specific embodiments, the topical analgesic includes the emulsifier 2±0.4 wt. % lecithin.

In specific embodiments, the topical analgesic includes the emulsifier 2±0.4 wt. % hydroxylated lecithin.

In specific embodiments, the topical analgesic includes the polymeric binder Carbopol 980, carbomer, cetyl alcohol, stearic acid, carnauba wax, hydroxyethyl cellulose, guar gum, xanthan gum, gelatin, magnesium aluminum silicate, silica, bentonite, cetyl palmitate, ammonium acryloyldimethyltaurate, cetearyl alcohol, glucose-D, hectorite gel, stearyl palmitate, gum arabic, hydroxypropyl starch phosphate, tapioca starch, acrylates octylacrylamide copolymer, carbomer 940, polyamide 3, castor wax, hydroxypropyl methylcellulose, *caesalpinia spinosa* gum, *brassica* alcohol, carbomer 980 QD, sodium stearate, polyhydroxystearic acid, tribehenin, arrowroot starch, rice starch, candelilla wax, beeswax, ozokerite wax, sunflower wax, PEG-ISO distearate, polyacrylate crosspolymer-6, acrylates C10-30 alkyl acrylate crosspolymer, hydroxypropyl guar, cyclopentasiloxane (silicone gel), or any combination thereof.

In specific embodiments, the topical analgesic includes the polymeric binder Carbopol 980.

In specific embodiments, the topical analgesic includes the polymeric binder 1.4±0.28 wt %.

In specific embodiments, the topical analgesic includes the polymeric binder 1.4±0.28 wt. % Carbopol 980.

In specific embodiments, the topical analgesic includes a solubility oil for a cannabinoid.

In specific embodiments, the topical analgesic includes a solubility oil for a cannabinoid isolate.

In specific embodiments, the topical analgesic includes a solubility oil for a CBD isolate.

In specific embodiments, the topical analgesic includes a solubility oil which is hemp oil.

In specific embodiments, the topical analgesic includes 1±0.2 wt. % solubility oil (e.g., hemp oil).

In specific embodiments, the topical analgesic includes a cannabinoid is in the form of hemp extract.

In specific embodiments, the topical analgesic includes a cannabinoid as 0.32±0.08 wt. % hemp extract.

In specific embodiments, the topical analgesic includes an anti-oxidant.

In specific embodiments, the topical analgesic includes the anti-oxidant tocopherol (vitamin E), tocopheryl acetate (vitamin E acetate), anthocyanins, proanthocyanins, alpha-lipoic acid, catechins, retinal (vitamin A), beta-carotene (vitamin A), Coenzyme Q10, chlorogenic acid, curcumin, vitamin C, theograndin, luteolin, acetophenone derivatives, monoterpenes, sesquiterpenes, triterpenes, phytosterols, ferulic acid, lycopene, or any combination thereof.

In specific embodiments, the topical analgesic includes an anti-oxidant in 0.1±0.02 wt. %.

In specific embodiments, the topical analgesic includes the anti-oxidant tocopheryl.

In specific embodiments, the topical analgesic includes the anti-oxidant 0.1±0.02 wt. % tocopheryl.

In specific embodiments, the topical analgesic includes the anti-oxidant tocopheryl acetate.

In specific embodiments, the topical analgesic includes the anti-oxidant 0.1±0.02 wt. % tocopheryl acetate.

In specific embodiments, the topical analgesic includes a preservative.

In specific embodiments, the topical analgesic includes the preservative butylparaben, ethylparaben, methylparaben, propylparaben, sorbic acid, benzyl alcohol, salicylic acid, formaldehyde, tetrasodium ethylenediaminetetra-acetic acid (EDTA), neroli hydrosol, phenoxyethanol, ethylhexylglycerin, methylisothiazolinone, methylchloroisothiazolinone, citric acid, sodium benzoate, tetrasodium glutamate diacetate, or any combination thereof.

In specific embodiments, the topical analgesic includes the preservative in 0.1±0.02 wt. %.

In specific embodiments, the topical analgesic includes the preservative sodium benzoate.

In specific embodiments, the topical analgesic includes the preservative 0.1±0.02 wt. % sodium benzoate.

In specific embodiments, the topical analgesic includes a microcirculation stimulant.

In specific embodiments, the topical analgesic includes the microcirculation stimulant caffeine.

In specific embodiments, the topical analgesic includes the microcirculation stimulant 1.5±0.3 wt. % caffeine.

In specific embodiments, the topical analgesic includes a pH adjusting agent.

In specific embodiments, the topical analgesic includes 1.5±0.3 wt. % pH adjusting agent.

In specific embodiments, the topical analgesic includes the pH adjusting agent sodium bicarbonate.

In specific embodiments, the topical analgesic includes the pH adjusting agent 1.5±0.3 wt. % sodium bicarbonate.

In specific embodiments, the topical analgesic includes an herbal active ingredient.

In specific embodiments, the topical analgesic includes an herbal active ingredient that is a natural topical pain remedy.

In specific embodiments, the topical analgesic includes 1.25±0.25 wt. % herbal active ingredient that is a natural topical pain remedy.

In specific embodiments, the topical analgesic includes white willow bark extract as an herbal active ingredient.

In specific embodiments, the topical analgesic includes 1.25±0.25 wt. % white willow bark extract as an herbal active ingredient.

In specific embodiments, the topical analgesic includes salicin as an herbal active ingredient, wherein the salicin is present as white willow bark extract.

In specific embodiments, the topical analgesic includes 1.25±0.25 wt. % salicin as an herbal active ingredient, wherein the salicin is present as white willow bark extract.

In specific embodiments, the topical analgesic includes menthol, cannabidiol (CBD), carbopol, lecithin, caffeine anhydrous, salicin, organic hemp oil, sodium benzoate, tocopheryl acetate, sodium bicarbonate, and water.

In specific embodiments, the topical analgesic includes menthol in 2.5±0.5 wt. %.

In specific embodiments, the topical analgesic includes cannabidiol (CBD) as 0.32±0.08 wt. % organic hemp extract or 0.35±0.08 wt. % organic hemp extract.

In specific embodiments, the topical analgesic is a topical analgesic cream.

In specific embodiments, the topical analgesic cream includes: menthol, cannabidiol (CBD), carbopol, lecithin, caffeine anhydrous, salicin, organic hemp oil, sodium benzoate, tocopheryl acetate, sodium bicarbonate, and water.

In specific embodiments, the topical analgesic cream includes menthol in 2.5±0.5 wt. %.

In specific embodiments, the topical analgesic cream includes cannabidiol (CBD) as organic hemp extract, in 0.32±0.1 wt. %.

In specific embodiments, the topical analgesic cream includes carbopol in 1.4±0.3 wt. %.

In specific embodiments, the topical analgesic cream includes lecithin in 2±0.4 wt. %.

In specific embodiments, the topical analgesic cream includes lecithin as hydroxylated lecithin, in 2±0.4 wt. %.

In specific embodiments, the topical analgesic cream includes caffeine anhydrous in 1.5±0.3 wt. %

In specific embodiments, the topical analgesic cream includes salicin as white willow bark extract, in 1.25±0.25 wt. %

In specific embodiments, the topical analgesic cream includes organic hemp oil in 1±0.2 wt. %.

In specific embodiments, the topical analgesic cream includes sodium benzoate in 0.1±0.02 wt. %.

In specific embodiments, the topical analgesic cream includes tocopheryl acetate in 0.1±0.04 wt. %.

In specific embodiments, the topical analgesic cream includes sodium bicarbonate in 1.5±0.3 wt. % In specific embodiments, the topical analgesic cream includes water in 88.33±5 wt. % or 88.30±5 wt. %.

In specific embodiments, the topical analgesic cream has a total THC content of less than 0.1 mg/mL, wherein the total THC content is defined as the amount of THCA*0.877, plus the amount of THC*1, expressed as:

Total THC content=(amount of THCA/mL*0.877)+(amount of THC/mL*1)<0.1 mg/mL.

In specific embodiments, the topical analgesic cream has a total THC content of less than 0.05 mg/mL, wherein the total THC content is defined as the amount of THCA*0.877, plus the amount of THC*1, expressed as:

Total THC content=(amount of THCA/mL*0.877)+(amount of THC/mL*1)<0.05 mg/mL.

In specific embodiments, the topical analgesic cream has a total THC content of less than 0.02 mg/mL, wherein the total THC content is defined as the amount of THCA*0.877, plus the amount of THC*1, expressed as:

Total THC content=(amount of THCA/mL*0.877)+(amount of THC/mL*1)<0.02 mg/mL.

In specific embodiments, the topical analgesic cream has a total THC content of less than 0.01 mg/mL, wherein the total THC content is defined as the amount of THCA*0.877, plus the amount of THC*1, expressed as:

Total THC content=(amount of THCA/mL*0.877)+(amount of THC/mL*1)<0.01 mg/mL.

In specific embodiments, the topical analgesic cream is substantially free from (a)-(e): (a) Tetrahydrocannabinol (THC), (b) Tetrahydrocannabinolic Acid (THCA), (c) Cannabidiolic Acid (CBDA), (d) Cannabinol (CBN), and (e) Cannabigerol (CBG), such that any of (a)-(e) present in the topical analgesic cream is present such that the topical analgesic cream includes each in no more than 0.1 mg/mL.

In specific embodiments, the topical analgesic cream is substantially free from (a)-(e): (a) Tetrahydrocannabinol (THC), (b) Tetrahydrocannabinolic Acid (THCA), (c) Cannabidiolic Acid (CBDA), (d) Cannabinol (CBN) and (e) Cannabigerol (CBG), such that any of (a)-(e) present in the topical analgesic cream is present such that the topical analgesic cream includes each in no more than 0.05 mg/mL.

In specific embodiments, the topical analgesic cream is substantially free from (a)-(e): (a) Tetrahydrocannabinol (THC), (b) Tetrahydrocannabinolic Acid (THCA), (c) Cannabidiolic Acid (CBDA), (d) Cannabinol (CBN) and (e) Cannabigerol (CBG), such that any of (a)-(e) present in the topical analgesic cream is present such that the topical analgesic cream includes each in no more than 0.01 mg/mL.

In specific embodiments, the topical analgesic cream is substantially free from (a)-(e): (a) Tetrahydrocannabinol (THC), (b) Tetrahydrocannabinolic Acid (THCA), (c) Cannabidiolic Acid (CBDA), (d) Cannabinol (CBN) (e) Cannabigerol (CBG), such any one or more of (a)-(e) present in the topical analgesic cream is present in a total, aggregate amount of no more than 0.2 mg/mL.

In specific embodiments, the topical analgesic cream is substantially free from (a)-(e): (a) Tetrahydrocannabinol (THC), (b) Tetrahydrocannabinolic Acid (THCA), (c) Cannabidiolic Acid (CBDA), (d) Cannabinol (CBN). (e) Cannabigerol (CBG), such any one or more of (a)-(e) present in the topical analgesic cream is present in a total, aggregate amount of no more than 0.1 mg/mL.

In specific embodiments, the topical analgesic cream is substantially free from (a)-(e): (a) Tetrahydrocannabinol (THC), (b) Tetrahydrocannabinolic Acid (THCA), (c) Cannabidiolic Acid (CBDA), (d) Cannabinol (CBN), (e) Cannabigerol (CBG), such any one or more of (a)-(e) present in the topical analgesic cream is present in a total, aggregate amount of no more than 0.05 mg/mL.

In specific embodiments, the topical analgesic cream is substantially free from (a)-(e): (a) Tetrahydrocannabinol (THC), (b) Tetrahydrocannabinolic Acid (THCA), (c) Cannabidiolic Acid (CBDA), (d) Cannabinol (CBN), (e) Cannabigerol (CBG), such any one or more of (a)-(e) present in the topical analgesic cream is present in a total, aggregate amount of no more than 0.02 mg/mL.

In specific embodiments, the topical analgesic cream includes: 2.5±0.5 wt. % menthol, 0.35±0.1 wt. % cannabidiol (CBD), 1.4±0.3 wt. % carbopol 980 NF, 2±0.4 wt. % lecithin, 1.5±0.3 wt. % caffeine anhydrous, 1.25±0.25 wt. % salicin (98 wt. % pure), 1±0.2 wt. % organic hemp oil, 0.1±0.02 wt. % sodium benzoate, 0.1±0.02 wt. % tocopheryl acetate, 1.5±0.3 wt. % sodium bicarbonate, and 88.30±5 wt. % water.

In specific embodiments, the topical analgesic cream includes: 2.5±0.5 wt. % menthol, 0.32±0.1 wt. % cannabidiol (CBD), 1.4±0.3 wt. % carbopol 980 NF, 2±0.4 wt. % lecithin, 1.5±0.3 wt. % caffeine anhydrous, 1.25±0.25 wt. % salicin (98 wt. % pure), 1±0.2 wt. % organic hemp oil, 0.1±0.02 wt. % sodium benzoate, 0.1±0.02 wt. % tocopheryl acetate, 1.5±0.3 wt. % sodium bicarbonate, and 88.33±5 wt. % water.

In specific embodiments, the topical analgesic cream includes: 2.5±0.5 wt. % menthol, 0.35±0.1 wt. % cannabidiol (CBD), 1.4±0.3 wt. % carbopol 980 NF, 2±0.4 wt. % hydroxylated lecithin, 1.5±0.3 wt. % caffeine anhydrous, 1.25±0.25 wt. % salicin (98 wt. % pure), 1±0.2 wt. % organic hemp oil, 0.1±0.02 wt. % sodium benzoate, 0.1±0.02 wt. % tocopheryl acetate, 1.5±0.3 wt. % sodium bicarbonate, and 88.30±5 wt. % water.

In specific embodiments, the topical analgesic cream includes: 2.5±0.5 wt. % menthol, 0.32±0.1 wt. % cannabidiol (CBD), 1.4±0.3 wt. % carbopol 980 NF, 2±0.4 wt. % hydroxylated lecithin, 1.5±0.3 wt. % caffeine anhydrous, 1.25±0.25 wt. % salicin (98 wt. % pure), 1±0.2 wt. % organic hemp oil, 0.1±0.02 wt % sodium benzoate, 0.1±0.02 wt. % tocopheryl acetate, 1.5±0.3 wt. % sodium bicarbonate, and 88.33 t 5 wt. % water.

In specific embodiments, the topical analgesic cream roll-on includes: 2.5±0.5 wt. % menthol; 84.40±5 wt. % USP water; 3.00±0.6 wt. % Isopropyl Alcohol; 0.90±0.1 wt. % Carbopol 980 NF; 2.00±0.04 wt. % Lecithin; 1.00±0.2 wt % Organic Hemp Oil; 1.00±0.2 wt % Cannabinoid (CBD isolate 99%); 1.50±0.3 wt % Caffeine Anhydrous; 1.50±0.3 wt. % Salicin, 98%; 0.40±0.08 wt. % Sodium Benzoate; 0.10±0.02 wt. % Potassium Sorbate; 0.20±0.04 wt. % Tocopheryl Acetate; and 1.50±0.30 wt. % Sodium Bicarbonate.

In specific embodiments, the topical analgesic cream roll-on includes: 2.5±0.5 wt. % menthol; 84.40±2.5 wt. % USP water; 3.00±0.3 wt % Isopropyl Alcohol; 0.90±0.05 wt. % Carbopol 980 NF; 2.00±0.02 wt. % Lecithin; 1.00±0.1 wt. % Organic Hemp Oil; 1.00±0.1 wt % Cannabinoid (CBD isolate 99%); 1.50±0.15 wt % Caffeine Anhydrous; 1.50±0.15 wt. % Salicin, 98%; 0.40±0.04 wt. % Sodium Benzoate; 0.10±0.01 wt. % Potassium Sorbate; 0.20±0.02 wt % Tocopheryl Acetate; and 1.50±0.15 wt % Sodium Bicarbonate.

In specific embodiments, the topical analgesic cream is formulated as 30±10 mL cream for use in an airless pump bottle with a protective cap and pump lid.

In specific embodiments, the topical analgesic cream is formulated as 50±15 mL cram for use in an airless pump bottle with a protective cap and pump lid.

In specific embodiments, the topical analgesic cream is formulated as 50±15 mL cream for use in a roll-on with a protective cap.

In specific embodiments, the topical analgesic cream is formulated as 30±15 mL cream for use in a roll-on with a protective cap.

In specific embodiments, the topical analgesic cream described herein is used for the temporary relief of minor aches and pains of muscles and joints.

In specific embodiments, a method for the temporary relief of minor aches and pains of muscles and joints is provided, wherein the method includes topically administering to the affected areas of a subject in need thereof the topical analgesic cream described herein.

In specific embodiments, the minor aches and pains of muscles and joints is associated with at least one of: simple backache, sore muscles, muscle fatigue, muscle stiffness, joint stiffness, arthritis, muscle strains, bursitis, tendonitis, bruises, contusion, cramps, and sprain.

In specific embodiments, the topical analgesic cream provides a cooling sensation.

In specific embodiments, the topical analgesic cream includes provides cooling pain relief.

In specific embodiments, the topical analgesic cream alleviates discomfort resulting from strenuous athletic training.

In specific embodiments, the topical analgesic cream aids in recovery from strenuous athletic training.

In specific embodiments, the topical analgesic cream is applied to a clean and dry topical skin surface of the subject.

In specific embodiments, the topical analgesic cream is applied to at least one of the back, neck, shoulder, knee, elbow, foot, ankle, leg, arm, hand, and wrist of the subject.

In specific embodiments, the topical analgesic cream is applied up to four times a day.

In specific embodiments, the topical analgesic cream is applied every 4-6 hours.

In specific embodiments, the topical analgesic cream is topically applied to an affected area and rubbed in.

In specific embodiments, the topical analgesic cream is topically applied to an affected area and rubbed in, and repeated every 4-6 hours.

In specific embodiments, after topically administering the topical analgesic cream to the subject, the method further includes rubbing or massaging the topical analgesic over the affected areas until thoroughly absorbed into the skin.

In specific embodiments, the topical analgesic cream is administered to a subject at least 12 years old.

In specific embodiments, the topical analgesic cream is administered to a subject at least 12 years old.

In specific embodiments, after the administration, the hands are washed with soap and water.

In specific embodiments, a method of manufacturing a topical analgesic is provided.

In specific embodiments, a method of manufacturing a topical analgesic cream is provided.

In specific embodiments, a method of manufacturing a topical analgesic is provided, wherein the method includes: (a) dissolving CBD in hemp oil to obtain a hemp mixture; (b) contacting menthol, caffeine anhydrous, white willow bark extract (salicin 98%), sodium benzoate, and tocopheryl acetate to obtain a dry mixture; (c) contacting Carbopol 980 NF and water until the Carbopol 980 NF is dissolved in the water or is dispersed throughout the water, to obtain a Carbopol mixture; (d) contacting lecithin (e.g., hydroxylated lecithin), water, and the dissolved CBD to form a first mixture; (e) contacting the hemp mixture, the dry mixture, and the Carbopol mixture to form a second mixture; (f) contacting sodium bicarbonate and the second mixture.

In specific embodiments, a method of manufacturing a topical analgesic is provided, which is a method for forming a cream.

In specific embodiments, a method of manufacturing a topical analgesic is provided, which is a method for forming a topical analgesic cream.

In specific embodiments, a method of manufacturing a topical analgesic is provided, wherein the CBD is present as a CBD distillate, a CBD isolate, or a combination thereof.

In specific embodiments, a method of manufacturing a topical analgesic is provided, wherein the dissolving of the CBD in the hemp oil is carried out at a temperature above 25° C.

In specific embodiments, a method of manufacturing a topical analgesic is provided, wherein the dissolving of the CBD in the hemp oil is carried out at a temperature of 25-100° C.

In specific embodiments, a method of manufacturing a topical analgesic is provided, wherein the contacting of the menthol, the caffeine anhydrous, the white willow bark extract (salicin 98%), the sodium benzoate, and the tocopheryl acetate to obtain the dry mixture.

In specific embodiments, a method of manufacturing a topical analgesic is provided, wherein the contacting of the Carbopol 980 NF the water is carried out with a high-speed mixer.

In specific embodiments, a method of manufacturing a topical analgesic is provided, wherein the first mixture is an encapsulated mixture.

In specific embodiments, a method of manufacturing a topical analgesic is provided, wherein the first mixture is an encapsulated mixture including the lecithin, the water, and the dissolved CBD.

In specific embodiments, a method of manufacturing a topical analgesic is provided, wherein the contacting of the lecithin, the water, and the dissolved CBD is carried out with a high speed mixer.

In specific embodiments a method of manufacturing a topical analgesic is provided, wherein the contacting of the hemp mixture, the dry mixture, and the Carbopol mixture to firm a second mixture is carried out with a high speed mixer.

In specific embodiments, a method of manufacturing a topical analgesic is provided, wherein the contacting of the sodium bicarbonate and the second mixture is carried out while blending.

In specific embodiments a method of manufacturing a topical analgesic is provided, wherein the contacting of the sodium bicarbonate and the second mixture is carried out while blending at a high speed, until substantially no air bubbles are present.

In specific embodiments a method of manufacturing a topical analgesic is provided, wherein the contacting of the sodium bicarbonate and the second mixture is carried out while blending at a high speed, until the consistency of a cream is obtained.

In specific embodiments, a method of manufacturing a topical analgesic is provided, wherein the contacting of the sodium bicarbonate and the second mixture is carried out while blending at a high speed, until a substantially homogenous consistency is achieved.

EXAMPLES

Example 1

A. Analgesic Cream with CBD Isolate and Organic Hemp Oil
ACTIVE INGREDIENT: 2.5 wt. % Menthol
INACTIVE INGREDIENTS: USP Water, Carbopol 980 NF, Lecithin, 0.330 wt. % CBD Isolate (99 wt. % pure), 1.5 wt. % Caffeine Anhydrous, 1.25 wt. % Salicin (98 wt. % pure), Organic Hemp Oil, Sodium Benzoate, Tocopheryl Acetate, Sodium Bicarbonate.

B. Analgesic Cream Roll-On with CBD Isolate and Organic Hemp Oil
ACTIVE INGREDIENT: 2.5 wt. % Menthol
INACTIVE INGREDIENTS: USP Water, Isopropyl Alcohol, Carbopol 980 NF, Lecithin, Organic Hemp Oil, CBD Isolate 99%, Menthol, Caffeine Anhydrous, Salicin, 98%, Sodium Benzoate, Potassium Sorbate, Tocopheryl Acetate, and Sodium Bicarbonate.

Base Formulation (Production Examples 2-73)

Production Examples 2-73 below illustrate active ingredients (external analgesic agents) formulated with suitable inactive ingredients to provide various dosage forms (e.g., creams and lotions). As described herein, the formulations illustrated in Production Examples 2-73 can be formulated to further include a cannabinoid, terpene, flavonoid, or combination thereof.

Production Example 2

Analgesic Gel
ACTIVE INGREDIENT: Menthol USP 4%
INACTIVE INGREDIENTS: *Aloe Barbadensis* Leaf Extract, *Arnica Montana* Flower Extract, *Arctium Lappa* Root (Burdock) Extract, *Boswellia Carterii* Resin Extract, *Calendula Officinalis* Extract, Carbomer, *Camellia Sinensis* Leaf Extract, Camphor USP, Glycerin, Ilex *Paraguariensis* Leaf Extract (Green Tea), Isopropyl Alcohol, Isopropyl Myristate, *Melissa Officinalis* (Lemon Balm) Leaf Extract, Silicon Dioxide, Tocopheryl (Vitamin E) Acetate, Triethanolamine, Purified Water USP, Blue 1, Yellow 5.

Production Example 3

Analgesic Roll-On Gel
ACTIVE INGREDIENT: Menthol 4%
INACTIVE INGREDIENTS: *Aloe Barbadensis* Leaf Extract, *Arctium Lappa* Root (Burdock) Extract, *Arnica Montana* Flower Extract, *Boswellia Carterii* Resin Extract, *Calendula Officinalis* Extract, *Camellia Sinensis* Leaf Extract, Camphor, Carbomer, Glycerin, Ilex *Paraguariensis* Leaf Extract, Isopropyl Alcohol, Isopropyl Myristate, *Melissa Officinalis* (Lemon Balm) Leaf Extract, Silica, Tocopheryl (Vitamin E) Acetate, Triethanolamine, Water.

Production Example 4

Analgesic Spray
ACTIVE INGREDIENT: Menthol 10.5%
INACTIVE INGREDIENTS: Alcohol Denat., *Arnica Montana* Flower Extract, *Calendula Officinalis* Flower Extract, *Camellia Sinensis* Leaf Extract, *Chamomilla Recutita* (*Matricaria*) Flower Extract, Dimethyl Sulfone (MSM), *Echinacea Angustifolia* Extract, Ilex *Paraguariensis* Leaf Extract, Isopropyl Myristate, *Juniperus Communis* Fruit Extract, Water.

Production Example 5

Analgesic Cream
ACTIVE INGREDIENT: Menthol 10%
INACTIVE INGREDIENTS: Caprylic/Capric Triglyceride, Cetearyl Alcohol, Diazolidinyl Urea, Dimethicone, Gluconolactone, Glycerin, Glyceryl Stearate, Ilex *Paraguariensis* Leaf Extract, Iodopropynyl butylcarbamate, Polysorbate 60, Sodium Benzoate, Sodium Hydroxide, Sodium Stearoyl Lactylate, Tetrasodium EDTA, Tocopheryl Acetate, *Vitis Vinifera* (Grape) seed Oil, Water.

Production Example 6

Analgesic Patch
ACTIVE INGREDIENT: Menthol 5%
INACTIVE INGREDIENTS: *Aloe Barbadensis* Leaf Extract, *Arnica Montana* Flower Extract, *Boswellia Carterii* Resin Extract, *Camellia Sinensis* Leaf Extract, Diazolidinyl Urea, Dihydroxyaluminum Aminoacetate Glycerin, Iodopropynyl Butylcarbamate, Kaolin, Polyacrylic Acid, Polysorbate 80, Propylene Glycol, PVP, Sodium Polyacrylate, Tartaric Acid, Titanium Dioxide, Water.

Production Example 7

Analgesic On-the-go-singles (10-3 mL gel packets)
ACTIVE INGREDIENT: Menthol 4%
INACTIVE INGREDIENTS: *Aloe Barbadensis* Leaf Extract, Arnica Montana Flower Extract, *Arctium* Lapp Root (Burdock) Extract, *Boswellia* Carteri Resin Extract, *Calendula Officinalis* Extract, Carbomer, *Camellia Sinensis* (Green Tea) Leaf Extract, Camphor, Glycerin, LLex *Paraguariensis* Leaf Extract. Isopropyl Alcohol, Isopropyl Myristate, *Melissa Officinalis* (Lemon Balm) Leaf Extract, Silica, Tocopheryl (Vitamin E) Acetate, Triethanolamine, Water, Blue 1, Yellow 5.

Production Example 8

Analgesic Gel pump
ACTIVE INGREDIENT: Menthol 4%
INACTIVE INGREDIENTS: *Aloe Barbadensis* Leaf Extract, *Arnica Montana* Flower Extract, *Arctium Lappa* Root (Burdock) Extract, *Boswellia Carterii* Resin Extract, *Calendula Officinalis* Extract, Carbomer, *Camellia Sinensis* (Green Tea) Leaf Extract, Camphor, Glycerin, Ilex *Paraguariensis* Leaf Extract, Isopropyl Alcohol, Isopropyl Myristate, *Melissa Officinalis* (Lemon Balm) Leaf Extract, Silica, Tocopheryl (Vitamin E) Acetate, Triethanolamine, Water, Blue 1, Yellow 5.

Production Example 9

Analgesic Cream
ACTIVE INGREDIENTS: Camphor 4%, Menthol 10%, Methyl salicylate 30%
INACTIVE INGREDIENTS: carbomer, disodium EDTA, glyceryl stearate SE, lanolin, polysorbate 80, potassium hydroxide, stearic acid, triethanolamine, water.

Production Example 10

Analgesic Cream
ACTIVE INGREDIENTS: Menthol 10%, Methyl salicylate 15%
INACTIVE INGREDIENTS: cetyl alcohol, glycerin, glyceral stearate, isopropyl palmitate, methylparaben, phenoxyethanol, potassium cetyl phosphate, potassium hydroxide, propylparaben, stearic acid, water, xantham gum.

Production Example 11

Analgesic Gel
ACTIVE INGREDIENT: Menthol 2.5%
INACTIVE INGREDIENTS: water, isopropyl alcohol, PEG-40 hydrogenated castor oil, carbomer, isoceteth-20, sodium hydroxide, DMDM hydantoin, camphor.

Production Example 12

Analgesic Patch
ACTIVE INGREDIENT: Menthol 5%
INACTIVE INGREDIENTS: calcined kaolin, cellulose gum, glycerin, methyl acrylate/2-ethylhexyl acrylate copolymer, methylparaben, polyacrylic acid, polysorbate 80, propylparaben, silica, sodium polyacrylate, sodium polyacrylate starch, sorbitan oleate, sorbitol, tartaric acid, titanium dioxide, water.

Production Example 13

Analgesic Gel
ACTIVE INGREDIENT: Menthol 5%
INACTIVE INGREDIENTS: water, ethanol, isopropanol, glycerin, polysorbate 60, carbomer, ethylhexyl isononanoate, aminomethyl propanol, disteareth-75 IPDI, camphor, PEG-7 caprylic/capric glycerides, blue 1.

Production Example 14

Analgesic Cream
ACTIVE INGREDIENTS: Menthol 10%, Methyl salicylate 15%
INACTIVE INGREDIENTS: Cetyl Alcohol, glycerin, Glyceryl Monostearate, Isopropyl Palmitate, Methylparaben, Phenoxyethanol, Potassium Cetyl Phosphate, Potassium Hydroxide, Propylparaben, Stearic Acid, Water, Xanthan Gum.

Production Example 15

Analgesic Gel
ACTIVE INGREDIENT: Menthol 2.5%
INACTIVE INGREDIENTS: camphor, carbomer, DMDM hydantoin, isoceteth-20, isopropyl alcohol, PEG-40 hydrogenated castor oil, sodium hydroxide, water.

Production Example 16

Analgesic Cream
ACTIVE INGREDIENTS: Camphor 4%, Menthol 10%, Methyl salicylate 30%
INACTIVE INGREDIENTS: carbomer, Disodium EDTA, glyceryl stearate se, lanolin, polysorbate 80, potassium hydroxide, purified water, stearic acid, Triethanolamine.

Production Example 17

Analgesic Gel
ACTIVE INGREDIENT: Menthol 2%
INACTIVE INGREDIENTS: water, isopropyl alcohol, PEG-40 hydrogenated castor oil, carbomer, isoceteth-20, sodium hydroxide, DMDM hydantoin, camphor.

Production Example 13

Analgesic Gel
ACTIVE INGREDIENT: Menthol 5%
INACTIVE INGREDIENTS: Alcohol, aminomethyl propanol, camphor, carbomer, disteareth-75 IPDI, ethylhexyl isononanoate, FD&C blue no. 1, glycerin, isopropyl alcohol, PEG-7 caprylic/capric glycerides, polysorbate 60, propylene glycol, water.

Production Example 19

Analgesic Patch
ACTIVE INGREDIENT: Menthol 5%
INACTIVE INGREDIENTS: calcined kaolin, cellulose gum, glycerin, methyl acrylate/2-ethylhexyl acrylate copolymer, methylparaben, polyacrylic acid, polysorbate 80, propylparaben, silica, sodium polyacrylate, sodium polyacrylate starch, sorbitan oleate, sorbitol, tartaric acid, titanium dioxide, water.

Production Example 20

Analgesic Cream
ACTIVE INGREDIENTS: Lidocaine HCl 4%, Menthol 1%
INACTIVE INGREDIENTS: Acrylates/C10-30 alkyl acrylate crosspolymer, *aloe barbadensis* leaf juice, aminomethyl propanol, C30-45 alkyl cetearyl dimethicone crosspolymer, caprylyl methicone, cetearyl alcohol, ceteth- 20 phosphate, dicetyl phosphate, dimethicone, disodium EDTA, ethylhexylglycerin, glyceryl stearate, hydroxyethyl acrylate/sodium acryloyldimethyl taurate copolymer, isohexadecane, methylparaben, polysorbate 60, SD alcohol 40 (15%), steareth-21, water.

Production Example 21

Analgesic Patch
ACTIVE INGREDIENTS: Lidocaine 4%, Menthol 1%
INACTIVE INGREDIENTS: Aluminum glycinate, aluminum hydroxide, cellulose gum, glycerin, methylparaben, PEG-40 hydrogenated castor oil, polyacrylic acid, polysorbate 80, propylene glycol, *Ricinus communis* (castor) seed oil, sillica, sodium polyacrylate, tartaric acid, titanium dioxide, urea, water.

Production Example 22

Analgesic Cream
ACTIVE INGREDIENTS: Lidocaine HCl 4%, Menthol 1%
INACTIVE INGREDIENTS: acrylates/C10-30 alkyl acrylate crosspolymer, *aloe barbadensis* leaf juice, aminomethyl propanol, C30-45 alkyl cetearyl dimethicone crosspolymer, caprylyl methicone, cetaryl alcohol, ceteth-20 phosphate, discetyl phosphate, dimethicone, disodium EDTA, ethylhexylglycerin, glyceryl stearate, hydroxyethyl acrylate/sodium acryloyldimethyl taurate copolymer, isohexadecane, methylparaben, polysorbate 60, SD alcohol 40 (15%), Steareth-21, water.

Production Example 23

Analgesic Cream
ACTIVE INGREDIENTS: Camphor 11%, Menthol 16%
INACTIVE INGREDIENTS: acrylates/C10-30 alkyl acylate crosspolymer, alantoin, *Aloe bartedensis* leaf juice, cetyl alcohol, disopropyl adipate, disodium EDTA, ethoxygigycol, fragrance, glycerin, glycoryl dilaurate, glyceryl stearate, menthyl lactate, methylcaraben, PEG-150 stearate, pentylene glycol, 4-t-butylcyclohexanol, phenoxyethanol, polysorbate 80, propanedlol, SD alcohol 40 (5% w/w), *Glycine soja* (soybean) sterols, steareth-21, stearic acid, Idethanolamine, water, xanthan gum (309-018).

Production Example 24

Analgesic Roll-on
ACTIVE INGREDIENT: Menthol 16%
INACTIVE INGREDIENTS: acrylates/C10-30 alkyl acrylate crosspolymer, capsaicin, glycerin, isopropyl myristate, propylene glycol, SD alcohol 40 (30%), triethanolamine, water (245-256).

Production Example 25

Analgesic Cream
ACTIVE INGREDIENTS: Menthol 10% Methyl Salicylate 30%
INACTIVE INGREDIENTS: carbomer, cetyl esters, emulsifying wax, oleth-3 phosphate, stearic acid, triethanolamine, water (245-110).

Production Example 26

Analgesic Spray
ACTIVE INGREDIENT: Menthol 16%
INACTIVE INGREDIENTS: glycerin, propylene glycol, SD alcohol 40-2 (55%), water.

Production Example 27

Analgesic Patch
ACTIVE INGREDIENT: Menthol 7.5%
INACTIVE INGREDIENTS: glyceryl hydrogenated rosinate, hydrated silica, mineral oil, PEG-400, polyisobutene, styrene/isoprene copolymer.

Production Example 28

Analgesic Gel
ACTIVE INGREDIENT: Menthol 2.5%
INACTIVE INGREDIENTS: allantoin, *aloe barbadensis* leaf juice, carbomer, DMDM hydantoin, glycerin, methylparaben, phenoxyethanol, propylparaben, SD alcohol 40-2 (15.47%), steareth-2, steareth-21, triethanolamine, water (245-135).

Production Example 29

Analgesic Balm
ACTIVE INGREDIENTS: Menthol 7.6%, Methyl salicylate 29%
INACTIVE INGREDIENTS: paraffin, white petrolatum (245-109).

Production Example 30

Analgesic Patch
ACTIVE INGREDIENT: Menthol 5%
INACTIVE INGREDIENTS: acrylic acid, aluminum hydroxide, carmellose sodium, 2-ethylhexyl acrylate, glycerin, isopropyl myristate, methyl acrylate, nonoxynol-30, polyacrylate, polyacrylic acid, polysorbate 80, sorbitan sesquioleate, starch, talc, tartaric acid, titanium dioxide, water (245-114).

Production Example 31

Analgesic Lotion
ACTIVE INGREDIENTS: Camphor 4%, Menthol 16%
INACTIVE INGREDIENTS: acrylates/C10-C30 alkyl acrylate crosspolymer, capsaicin, cetyl alcohol, citric acid, disopropyl adipate, disodium EDTA, ethoxydiglycol, glycerin, glyceryl dilaurate, glyceryl stearate, *Glycine soja* sterals, menthyl lactate, methylparaben, PEG-150 stearate, phenoxyethanol, polysorbate 80, propylene glycol, SD alcohol 40 (15% w/w), steareth-2, steareth-21, tocopheryl acetate, triethanolamine, water, xanthan gum (283-106).

Production Example 32

Analgesic Gel
ACTIVE INGREDIENT: Menthol 16%
INACTIVE INGREDIENTS: acrylates/C10-C30 alkyl acrylate crosspolymer, blue 1, glycerin, hydroxypropyl methylcellulose, propylene glycol, SD alcohol 40-2 (30%) triethanolamine, water (283-027).

Production Example 33

Analgesic Patch
ACTIVE INGREDIENT: Menthol 7.5%
INACTIVE INGREDIENTS: glyceryl hydrogenated rosinate, hydrated silica, mineral oil, PEG-400, polyisobutene, styrene/isoprene copolymer.

Production Example 34

Analgesic Stick
ACTIVE INGREDIENTS: Menthol 10%, Methyl Salicylate 30%
INACTIVE INGREDIENTS: carbomer, cetyl esters, emulsifying wax, oleth-3 phosphate, stearic acid, triethanolamine, water (245-110).

Production Example 35

Analgesic Cream
ACTIVE INGREDIENT: Trolamine Salicylate 10%
INACTIVE INGREDIENTS: aloe barbadensis leaf juice, cetyl alcohol, glycerin, methylparaben, mineral oil, potassium phosphate, propylparaben, stearic acid, triethanolamine, water (241-75).

Production Example 36

Analgesic Lotion
ACTIVE INGREDIENT: Trolamine Salicylate 10%
INACTIVE INGREDIENTS: aloe barbadensis leaf juice, cetyl alcohol, glyceryl stearate, isopropyl palmitate, lanolin, methylparaben, potassium phosphate, propylene glycol, propylparaben, sodiem lauryl sulfate, stearic acid, water (241-76).

Production Example 37

Analgesic Roll-On
ACTIVE INGREDIENT: Menthol 16%
INACTIVE INGREDIENTS: acrylates/C10-C30 alkyl acrylate crosspolymer, capsaicin, glycerin, isopropyl myristate, propylene glycol, SD alcohol 40 (30%), triethanolamine, water (245-256).

Production Example 38

Analgesic Gel
ACTIVE INGREDIENT: Menthol 10%
INACTIVE INGREDIENTS: acrylates/C10-30 alkyl acrylate crosspolymer, allantoin, aloe barbadensis leaf juice, capsaicin, DMDM hydantoin, fragrance, glycerin, methylparaben, phenoxyethanol, propylene glycol, propylparaben, SD alcohol 40-2 (15%), steareth-2, steareth-21, triethanolamine, water.

Production Example 39

Analgesic Get
ACTIVE INGREDIENT: Menthol 10%
INACTIVE INGREDIENTS: acrylates/C10-30 alkyl acrylate crosspolymer, allantoin, aloe barbadensis leaf juice, capsaicin, DMDM hydantoin, fragrance, glycerin, methylparaben, phenoxyethanol, propylene glycol, propylparaben, SD alcohol 40 (15%), steareth-2, steareth-21, triethanolamine, water.

Production Example 40

Analgesic Cream
ACTIVE INGREDIENT: Trolamine salicylate 10%
INACTIVE INGREDIENTS: aloe barbadensis leaf juice, cetyl alcohol, glycerin, methylparaben, mineral oil, potassium phosphate, propylparaben, stearic acid, triethanolamine, water.

Production Example 41

Analgesic Roll-On
ACTIVE INGREDIENT: Menthol 16%
INACTIVE INGREDIENT: acrylates/C10-30 alkyl acrylate crosspolymer, capsaicin, glycerin, isopropyl myristate, propylene glycol. SD alcohol 40 (30%) triethanolamine, water.

Production Example 42

Analgesic Cream
ACTIVE INGREDIENT: Lidocaine HCl 4%
INACTIVE INGREDIENTS: acylates/C10-30 alkyl acrylate crosspolymer, aloe barbadensis leaf juice, aminomethyl propanol, C30-45 alkyl cetearyl dimethicone crosspolymer, caprylyl methicone, cetearyl alcohol, ceteth-20 phosphate, dicetyl phosphate, dimethicone, disodium EDTA, ethylhexylglycerin, glyceryl stearate, methylparaben, SD alcohol 40 (15%), steareth-21, water.

Production Example 43

Analgesic Cream
ACTIVE INGREDIENT: Trolamine salicylate 10%
INACTIVE INGREDIENTS: aloe barbadensis leaf juice, cetyl alcohol, glycerin, methylparaban, mineral oil, potassium phosphate, propylparaban, stearic acid, triethanolamine, water.

Production Example 44

Analgesic Patch
ACTIVE INGREDIENT: Capsaicin 0.025%
INACTIVE INGREDIENTS: aluminum hydroxide, benzyl alcohol, cellulose gum, disodium EDTA, glycerin, isopropyl myristate, methyl acrylate/2-ethylhexyl acrylate copolymer, nonoxynol-30, polyacrylic acid, polysorbate 80, sodium polyacrylate, starch/acrylic acid graft copolymer sodium salt, talc, tartaric acid, titanium dioxide, tocopherol, water.

Production Example 45

Analgesic Gel
ACTIVE INGREDIENT: Capsaicin 0.025%
INACTIVE INGREDIENTS: acrylates/C10-30 alkyl acrylate crosspolymer, aloe barbadensis leaf juice, citric acid, disodium EDTA, ethylhexylglycerin, glycerin, methylparaben, propylene glycol, steareth-2, steareth-21, triethanodamine, water.

Production Example 46

Analgesic Patch
ACTIVE INGREDIENT: Lidocaine 4%
INACTIVE INGREDIENTS: aluminum glycinate, aluminum hydroxide, cellulose gum, glycerin, methylparaben, polyacrylic acid, polysorbate 80, propylene glycol, silica, sodium polyacrylate, tartaric acid, titanium dioxide, urea, water.

Production Example 47

Analgesic Patch
ACTIVE INGREDIENT: Lidocaine 4%
INACTIVE INGREDIENTS: aluminum glycinate, aluminum hydroxide, cellulose gum, glycerin, methylparaben, polyacrylic acid, polysorbate 80, propylene glycol, silica, sodium polyacrylate, tartaric acid, titanium dioxide, urea, water.

Production Example 48

Analgesic Liquid (roll-on)
ACTIVE INGREDIENT: Lidocaine HCl 4%
INACTIVE INGREDIENTS: acrylates/C10-30 alkyl acrylate crosspolymer, *aloe barbadensis* leaf juice, aminomethyl propanol, C30-45 alkyl cetearyl dimethicone crosspolymer, caprylyl methicone, cetearyl alcohol, ceteth-20 phosphate, dicetyl phosphate, dimethicone, disodium EDTA, ethylhexylglycerin, glyceryl stearate, hydroxyethyl acrylate/sodium acryloyldimethyl taurate copolymer, isohexadecane, methylparaben, polysorbate 60, SD alcohol 40 (15%), steareth-2, steareth-21, water.

Production Example 49

Analgesic Cream
ACTIVE INGREDIENT: Lidocaine HCl 4%
INACTIVE INGREDIENTS: acrylates/C10-30 alkyl acrylate crosspolymer, *aloe barbadensis* leaf juice, aminomethyl propanol, C30-45 alkyl cetearyl dimethicone crosspolymer, caprylyl methicone, cetearyl alcohol, ceteth-20 phosphate, dicetyl phosphate, dimethicone, disodium EDTA, ethylhexylglycerin, glyceryl stearate, methylparaben, SD alcohol 40 (15), steareth-21, water.

Production Example 50

Analgesic Cream
ACTIVE INGREDIENT: 10% Trolamine Salicylate
INACTIVE INGREDIENTS: blue 1, cetyl alcohol, fragrance, glycerin, methylparaben, mineral oil, potassium phosphate, propylparaben, stearic acid, triethanolamine, water, yellow 5.

Production Example 51

Analgesic Cream
ACTIVE INGREDIENTS: Methyl Salicylate 15%, Menthol 5%, Camphor 3%
INACTIVE INGREDIENTS: Diazolidinyl Urea Glycerin, Methyl Glucose Dioleate, Methyl Paraben, Poly (Methyl Vinyl Ether/Maleic Anhydride) Decadiene Crosspolymer, Propyl Paraben, Propylene Glycol, Purified Water, Triethanolmine.

Production Example 52

Analgesic Gel
ACTIVE INGREDIENTS: Methyl Salicylate 16%, Menthol 86
INACTIVE INGREDIENTS: Carbomer 940, Citric Acid Monohydate, FD&C Blue No. 1, Fragrance Active Fresh 1, Methylated Spirit, PEG-15 Cocamine, PPG-5 Ceteth-20, Propylene Glycol, Purified Water.

Production Example 53

Analgesic Spray
ACTIVE INGREDIENTS: Methyl Salicylate 25%, Menthol 16%, Camphor 7%
INACTIVE INGREDIENTS: Ethanol (Dehydrated Alcohol), Liquefied Petroleum Gas.

Production Example 54

Analgesic Patch
ACTIVE INGREDIENTS: Camphor 230 mg/patch, Menthol 70 mg/patch
INACTIVE INGREDIENTS: *Capsicum* Extract, *Eucalyptus* Oil. Glycerin, *Mentha* Oil, Polyacrylic Acid, Polysorbate 80, Sodium Carboxymethylcellulose, Sodium Polyacrylate, Sorbitan Monooleate, Sorbitol, Tartaric Acid, Water.

Production Example 55

Analgesic Liniment
ACTIVE INGREDIENTS: Methyl Salicylate 28%, Menthol 16%
INACTIVE INGREDIENTS: *Eucalyptus* Oil, Spike Lavender Oil, Light Mineral Oil.

Production Example 56

Analgesic Cream
ACTIVE INGREDIENTS: Camphor 11%, Menthol 11%
INACTIVE INGREDIENTS: Cajuput Oil, Chondroitin Sulfate, Cinnamon Oil, Clove Oil, Deionized Water, Dementholised Mint Oil, Diazolidinyl Urea, Glucosamine Sulfate, Methyl Paraben, Methylsulfonylmethane (MSM), PEG-120 Methyl Glucose Dioleate, Propyl Paraben, Propylene Glycol.

Production Example 57

Analgesic Cream
ACTIVE INGREDIENTS: Methyl Salicylate 15%, Menthol 5%, Camphor 3%
INACTIVE INGREDIENTS: Diazolidinyl Urea, Glycerin, Methyl Glucose Dioleate, Methyl Paraben, Poly (Methyl Vinyl Ether/Maleic Anhydride) Decadiene Crosspolymer, Propyl Paraben, Propylene Glycol, Purified Water, Triethanolamine.

Production Example 58

Analgesic Cream
ACTIVE INGREDIENTS: Camphor 11%, Menthol 10%
INACTIVE INGREDIENTS: Dementholised Mint Oil, Diazolidinyl Urea, *Eucalyptus* Oil, FD&C Blue 1, Glycerin, Lavender Fragrance, Methyl Glucose Dioleate Methylparaben, PVM/MA Decadiene Crosspolymer, Propylene Glycol, Propylparaben, Triethanolamine (TEA), Water.

Production Example 59

Analgesic Patch
ACTIVE INGREDIENTS: DL-Camphor 110 mg/patch, L-Menthol 33 mg/patch, *Capsicum* Extract 22 mg/patch
INACTIVE INGREDIENTS: Carboxymethylcellulose Sodium, *Eucalyptus* Oil, Glycerin, *Mentha* Oil, Methyl Acrylate and 2-Ethylhexyl Acrylate Copolymer, Purified Water, Polysorbate 80, PVA Solution, Silicon Dioxide, Sodium Polyacrylate, Sodium Polyacrylate Starch, Sorbitan Monooleate, Sorbitol Solution, Tartaric Acid.

Production Example 60

Analgesic Ointment
ACTIVE INGREDIENTS: Camphor 1%, Menthol 10%
INACTIVE INGREDIENTS: Cajuput Oil, *Cassia* Oil, Clove Oil, Dementholised Mint Oil and Paraffin Petrolatum.

Production Example 61

Analgesic Ointment
ACTIVE INGREDIENTS: Camphor 11%, Menthol 11%
INACTIVE INGREDIENTS: Cajuput Oil, *Cassia* Oil, Clove Oil, Dementholized Mint Oil and Paraffin Petrolatum.

Production Example 62

Analgesic Patch
ACTIVE INGREDIENTS: Methyl Salicylate 10%, Menthol 3%
INACTIVE INGREDIENTS: Styrene-Isoprene-Styrene Block Copolymer, Petrolatum Hydrocarbon Resin, Mineral Oil.

Production Example 63

Analgesic Ointment
ACTIVE INGREDIENTS: Camphor 11%, Menthol 8%
INACTIVE INGREDIENTS: Cajuput Oil, Clove Oil, Dementholised Mint Oil and Paraffin Petrolatum.

Production Example 64

Analgesic Gel
ACTIVE INGREDIENT: Menthol 2%
INACTIVE INGREDIENTS: ammonium hydroxide, carbomer, cupric sulfate, FD&C blue no. 1, isopropyl alcohol, magnesium sulfate, purified water, sodium hydroxide, thymol.

Production Example 65

Analgesic Gel
ACTIVE INGREDIENT: Menthol 7%
INACTIVE INGREDIENTS: allantoin, *aloe barbadensis* leaf juice, carbomer, *Eucalyptus globulus* leaf oil, glycerin, *Mentha piperita* (peppermint) oil, methyl salicylate, SD alcohol 40 (15%), steareth-2, steareth-21, *Thymus vulgaris* (thyme) oil, tocopheryl acetate, triethanolamine, water.

Production Example 66

Analgesic Gel
ACTIVE INGREDIENT: Menthol 16%
INACTIVE INGREDIENTS: allantoin, *aloe barbadensis* leaf juice, carbomer, diisopropyl adipate, *Eucalyptus globulus* leaf oil, glycerin, *Mentha piperita* (peppermint) oil, methyl salicylate, SD alcohol 40 (15% w/w), steareth-2, steareth-21, *Thymus vulgaris* (thyme) oil, tocopheryl acetate, triethanolamine, water.

Production Example 67

Analgesic Gel
ACTIVE INGREDIENTS: Camphor 3.1%, Menthol 16%, Methyl salicylate 10%
INACTIVE INGREDIENTS: allantoin, *aloe barbadensis* leaf juice, carbomer, diisopropyl adipate, *Eucalyptus globulus* leaf oil, glycerin, *Mentha piperita* (peppermint) oil, SD alcohol 40 (15% w/w), steareth-2, steareth-21, *Thymus vulgaris* (thyme) oil, tocopheryl acetate, triethanolamine, water.

Production Example 68

Analgesic Cream
ACTIVE INGREDIENT: Capsaicin 0.035%
INACTIVE INGREDIENTS: benzyl alcohol, cetyl alcohol, glyceryl stearate, isopropyl myristate, PEG-40 stearate, petrolatum, sorbitol, water (238-9).

Production Example 69

Analgesic Cream
ACTIVE INGREDIENT: Capsaicin 0.1%
INACTIVE INGREDIENTS: benzyl alcohol, cetyl alcohol, glyceryl stearate, isopropyl myristate, PEG-40 stearate, petrolatum, sorbitol, water.

Production Example 70

Analgesic Gel
ACTIVE INGREDIENT: Capsaicin 0.025%, Menthol 10%
INACTIVE INGREDIENTS: acrylates/C10-30 alkyl acrylate crosspolymer, allantoin, *aloe barbadensis* leaf juice, DMDM hydantoin, fragrance, glycerin, methylparaben, phenoxyethanol, propylene glycol, propylparaben, SD alcohol 40-2 (15%), steareth-2, steareth-21, triethanolamine, water.

Production Example 71

Analgesic Liquid (roll-on)
ACTIVE INGREDIENT: Capsaicin 0.15%
INACTIVE INGREDIENTS: carbomer, glycerin, propylene glycol, SD alcohol 40-2 (35%), triethanolamine, water.

Production Example 72

Analgesic Cream
ACTIVE INGREDIENT: Camphor (3.1%)
INACTIVE INGREDIENTS: Acetylated Lanolin, Acrylates/C10-30 Alkyl Acrylates Crosspolymer, *Aloe vera*, C12-15 Alkyl Benzoate, Chondroitin Sulfate, Diazolidinyl Urea, Dimethicone, Dimethiconol Stearate, Disodium EDTA, dl Panthenol, Glucosamine Sulfate, Glycerin, Glycerol Stearate, Glycosaminoglycans, Hydroxylated Lanolin, Hydroxypropyl Methylcellulose, Iodopropynyl Butyl Carbamate, Methyl Gluceth-20, Methyl Glucose Sesquistearate, Peppermint Oil, Polysorbate 20, Potassium Carbomer, Purified Water, Tocopheryl Acetate (Vitamin E).

Production Example 73

Analgesic Cream

ACTIVE INGREDIENT: 2.5 wt. % Menthol

INACTIVE INGREDIENTS: 1.4 wt. % Carbopol 980 NF, 2 wt. % Lecithin, 1.5 wt. % Caffeine Anhydrous, 1.25 wt. % Salicin (98 wt. % pure), 1 wt. % Organic Hemp 00, 0.1 wt. % Sodium Benzoate, 0.2 wt. % Tocopheryl Acetate, 1.5 wt. % Sodium Bicarbonate, q.s. Water.

Production Example 74

Active ingredients (external analgesics)

Active ingredients (external analgesics) suitable for formulation with: (1) suitable inactive ingredients (excipients), and (2) a cannabinoid, terpene, flavonoid, or combination thereof, to provide various topical analgesic dosage forms (e.g., creams, gels, lotions, etc.).

TABLE A

| Ingredient | Dose | Min | Max |
| --- | --- | --- | --- |
| aspirin | | | |
| benzocaine | | 5 wt. % | 20 wt. % |
| benzyl alcohol | | 10 wt. % | 33 wt. % |
| butamben picrate | 1 wt. % | | |
| camphor | | 0.1 wt. % | 3 wt. % |
| camphor (when combined with phenol | 3 wt. % | | 10.80 wt. % |
| camphorated metacresol | camphor (3-10.8 wt. %) and metacresol (1-3.6 wt. %) | | |
| chloral hydrate | | | |
| chlorobutanol | | | |
| cyclomethycaine sulfate | | | |
| dibucaine | | 0.25 wt. % | 1 wt. % |
| dibucaine hydrochloride | | 0.25 wt. % | 1 wt. % |
| dimethisoquin hydrochloride | | 0.3 wt. % | 0.5 wt. % |
| diphenhydramine hydrochloride | | 1 wt. % | 2 wt. % |
| dyclonine hydrochloride | | 0.5 wt. % | 1 wt. % |
| eugenol | | | |
| hexylresorcinol | | | |
| hydrocortisone | | 0.25 wt. % | 1.0 wt. % |
| hydrocortisone (0.25-1 wt. %) | | | |
| hydrocortisone acetate | | 0.25 wt. % | 1.0 wt. % |
| hydrocortisone acetate (0.25-1.0 wt. %) | | | |
| juniper tar | | 1 wt. % | 5 wt. % |
| lidocaine | | 0.5 wt. % | 4 wt. % |
| lidocaine hydrochloride | | 0.5 wt. % | 4 wt. % |
| menthol | | 0.1 wt. % | 1 wt. % |
| methapyrilene hydrochloride | | | |
| obtundia surgical dressing | | | |
| phenol | 0.5-1.5 wt. % or 4.7 wt. % when combined with camphor | | |
| phenolate sodium | | 0.5 wt. % | 1.5 wt. % |
| pramoxine hydrochloride | | 0.5 wt. % | 1 wt. % |
| resorcinol | | 0.5 wt. % | 3 wt. % |
| salicylamide | | | |
| tetracaine | | 1 wt. % | 2 wt. % |
| tetracaine hydrochloride | | 1 wt. % | 2 wt. % |
| thymol | | | |
| tripelennamine hydrochloride | | 0.5 wt. % | 2 wt. % |

TABLE B

| ACTIVE | AMOUNT |
| --- | --- |
| Menthol | 2.5 wt. % |
| Menthol | 4 wt. % |
| Menthol | 5 wt. % |
| Menthol | 10.50 wt. % |
| Menthol | 10 wt. % |
| Menthol | 16 wt. % |
| Menthol | 7.0 wt. % |
| Menthol | 7.5 wt. % |
| Menthol | 2 wt. % |
| Menthol | 16 wt. % |
| Menthol/Methyl salicylate | 10 wt. %/15 wt. % |
| Menthol/Methyl salicylate | 10 wt. %/30 wt. % |
| Menthol/Methyl salicylate | 7.6 wt. %/29 wt. % |
| Menthol/Methyl salicylate | 8 wt. %/16 wt. % |
| Menthol/Methyl salicylate | 16 wt. %/28 wt. % |
| Menthol/Methyl salicylate | 3 wt. %/10 wt. % |
| Camphor | 3.10 wt. % |
| Camphor/Menthol | 11 wt. %/8 wt. % |
| Camphor/Menthol | 11 wt. %/16 wt. % |
| Camphor/Menthol | 4 wt. %/16 wt. % |
| Camphor/Menthol | 2.30 mg/70 mg |
| Camphor/Menthol | 11 wt. %/11 wt. % |
| Camphor/Menthol | 11 wt. %/10 wt. % |
| Camphor/Menthol/Methyl salicylate | 4 wt. %/10 wt.%/30 wt. % |
| Camphor/Menthol/Methyl salicylate | 3 wt. %/5 wt.%/15 wt. % |
| Camphor/Menthol/Methyl salicylate | 7 wt. %/16 wt.%/25 wt. % |
| Camphor/Menthol/Methyl salicylate | 3.1 wt. %/16 wt. %/10 wt. % |
| Camphor/Menthol/Capsicum | 110 mg/33 mg/22 mg |
| Trolamine salicylate | 10 wt. % |
| Lidocaine HCl/Menthol | 4 wt. %/1 wt. % |
| Lidocaine/Menthol | 4 wt. %/1 wt. % |
| Lidocaine HCl | 4 wt. % |
| Lidocaine | 4 wt. % |
| Capsaicin | 0.03 wt. % |
| Capsaicin | 0.035 wt. % |
| Capsaicin | 0.10 wt. % |
| Capsaicin | 0.15 wt. % |
| Capsaicin/Menthol | 0.025 wt. %/10 wt. % |
| Benzocaine | 10 wt. % |
| Benzocaine | 20 wt. % |
| Capsaicin | 0.025 wt. % |
| Capsaicin | 0.075 wt. % |
| Capsaicin/Lidocaine/Menthol/Methyl salicylate | 0.0375 wt. %/4 wt. %/10 wt. %/20 wt. % |
| Camphor | 11 wt. % |
| Camphor/Menthol | 0.2 wt. %/3.5 wt. % |
| Camphor/Menthol | 230 mg/70 mg |
| Camphor/Menthol | 5 wt. %/5 wt. % |
| Menthol | 1 wt. % |
| Menthol | 3.5 wt. % |
| Menthol | 8.00 wt. % |
| Camphor/Menthol/Mehyl salicylate | 3.1 wt. %/6 wt. %/10 wt. % |
| Camphor/Menthol/Capsicum extract | 80 mg/24 mg/16 mg |
| Camphor/Capsicum oleoresin/methyl salicylate | 0.62 wt. %/2.66 wt. %/3.35 wt. % |
| Methyl salicylate/capsaicin/menthol | 10 wt. %/25 wt. %/0.025 wt. % |
| Methyl salicylate/capsaicin/menthol | 20 wt. %/0.0375 wt. %/5 wt. % |
| Methyl salicylate/capsaicin/menthol | 20 wt. %/0.025 wt. %/10 wt. % |
| Lidocaine/Menthol/Capsaicin/Methyl salicylate | 4.5 wt. %/10 wt. %/0.0325 wt. %/27.5 wt. % |
| Lidocaine/Menthol/Capsaicin/Methyl salicylate | 0.5 wt. %/5 wt. %/0.0375 wt. %/2 wt. % |
| Lidocaine HCl | 0.50 wt. % |
| Lidocaine HCl | 2.00 wt. % |
| Lidocaine HCl | 2.5 wt. % |
| Lidocaine | 0.5 wt. % |
| Lidocaine | 1 wt. % |
| Lidocaine | 5.0 wt. % |
| Pramoxine hydrochloride | 1 wt. % |
| Tetracaine HCl | 4 wt. % |

TABLE C

| ACTIVE | DOSAGE FORM & STRENGTHS |
|---|---|
| Diclofenac | Tablet: 25 mg, 50 mg, 75 mg Gel: 11.6 mg/g |
| Diclofenac | Gel: 1 wt. % |
| Diclofenac | Patch 12 hr: 1.3 wt. % |
| Diclofenac | Patch 12 hr: 1.3 wt. % |
| Diclofenac sodium | Topical solution: 1.5 wt. % |
| diclofenac sodium and capsaicin oleoresin | Kit: Topical solution: 1.5 wt. % Diclofenac sodium (150 mL)/ Cream: 0.025 wt. % Capsaicin (273 mL) |
| Capsicum Oleoresin | Cream: 0.0625 wt. % (containing 0.025 wt. % capsaicin) |
| Buprenorphine Hydrochloride | Patch weekly/transdermal: 5 mcg/hr; 7.5 mcg/hr; 10 mcg/hr; 15 mcg/hr, 20 mcg/hr |
| Buprenorphine Hydrochloride | Patch weekly/transdermal: 5 mcg/hr; 7.5 mcg/hr; 10 mcg/hr; 15 mcg/hr, 20 mcg/hr |
| Fentanyl citrate or Hydrochloride | Patch (transdermal)-base: 12.5 mcg/hr (5s); 25 mcg/hr (5s), 37.5 mcg/hr (5s); 50 mcg/hr (5s), 62.5 mcg/hr (5s); 75 mcg/hr (5s), 87.5 mcg/hr (5s); 100 mcg/hr (5s) |
| Fentanyl Hydrochloride | Patch (transdermal): 12.5 mcg/hr (5s); 25 mcg/hr (5s), 50 mcg/hr (5s), 75 mcg/hr (5s), 100 mcg/hr (5s) |
| Fentanyl Hydrochloride | Patch: 40 mcg/actuation (6s) |
| Clonidine Hydrochloride | Patch (transdermal): 0.1 mg/24 hr; 0.2 mg/24 hr; 0.3 mg/24 hr |
| Clonidine Hydrochloride | Patch (transdermal): 0.1 mg/24 hr; 0.2 mg/24 hr; 0.3 mg/24 hr |
| Lidocaine hydrochloride | Jelly: 2 wt. % |
| Lidocaine hydrochloride | Topical ointment: 5 wt. % |
| Lidocaine hydrochloride | Cream: 38.8 mg in 1 g |
| Lidocaine hydrochloride | Jelly: 2 wt. % |
| Lidocaine hydrochloride | Topical solution: 4 wt. % |
| Lidocaine hydrochloride | Cream: 3 wt. % |
| Lidocaine hydrochloride | Cream: 3.25 wt. % |
| Lidocaine hydrochloride | Ointment: 5 wt. % |
| Lidocaine hydrochloride | Cream: 3.75 wt. % |
| Lidocaine hydrochloride | Lotion 3 wt. % |
| Lidocaine hydrochloride | Cream: 3.75 wt. % |
| Lidocaine hydrochloride | Gel: 4 wt. % (30 mL) |
| Lidocaine hydrochloride | Lotion: 3 wt. % |
| Lidocaine hydrochloride | Cream: 3 wt. % |
| Lidocaine hydrochloride | Ointment: 5 wt. % |
| Lidocaine hydrochloride | Ointment: 5 wt. % |
| Lidocaine hydrochloride | Lotion: 3 wt. % |
| Lidocaine hydrochloride | Ointment: 5 wt. % |
| Lidocaine hydrochloride | Gel: 4 wt. % |
| Lidocaine, acetamide | Ointment: 5 wt. % |
| diclofenac sodium and capsaicin | Kit: Topical solution: 1.5 wt. % diclofenac sodium (150 mL)/Cream: 0.025 wt. % Capsaicin |
| diclofenac sodium and capsaicin | Kit: Topical solution: 1.5 wt. % diclofenac sodium (150 mL)/Cream: 0.025 wt. % Capsaicin |
| diclofenac sodium and capsaicin | Kit: Topical solution: 1.5 wt. % diclofenac sodium (150 mL)/Cream: 0.025 wt. % Capsaicin |
| diclofenac sodium, capsaicin | Kit: Topical solution: 1.5 wt. % diclofenac sodium (150 mL)/Cream: 0.025 mg in 0.001 g Capsaicin |
| Capsaicin | Patch: 8 wt. % |
| Capsaicin/Lidocaine/Menthol | Cream: Lidocaine 5 wt. %, Menthol 3 wt. % and Capsaicin 0.05 wt. % |
| camphor, menthol, tetracaine | Topical spray: Camphor 3 wt. %, Menthol 1 wt. %, Tetracaine HCl 2 wt. % |
| Benzocaine | Gel: 20 wt. % |
| Benzocaine | Gel: 20 wt. % |
| Pramoxine hydrochloride/ hydrocortisone acetate | Topical aersol: 1 wt. % each |
| Methyl salicylate/menthol/capsaicin | Ointment: 20 wt. % MS/7 wt. % menthol/0.05 wt. % capsaicin |

TABLE D

| ACTIVE | AMOUNT |
|---|---|
| Aluminum hydroxide | 0.15 to 5 wt. % |
| Aspirin | 162 mg |
| Benzyl alcohol | 10 to 33 wt. % |
| Camphorated metacresol | 3 to 10.8 wt. % camphor 1 to 3.6 wt. % metacresol |
| Chloral hydrate | |
| Chlorobutanol | |
| Cyclomethycaine sulfate | |
| Eugenol | 85 wt. % |
| Hexylresorcinol | 0.1 wt. % |
| Methapyrilene hydrochloride | |
| Salicylamide | 152 mg |
| Tetracaine | 1 to 2 wt. % |
| Thymol | |
| Eucalyptus oil | 0.1 wt. %-15 wt. % |
| Allyl isothiocyanate | 0.5 to 5 wt. % |
| Ammonia solution, strong (ammonia water, strong) | 1 to 2.5 wt. % |
| Bismuth sodium tartrate | |
| Camphor (exceeding 3 wt. %) | 0.1 to 3 wt. %; up to 25 wt. % |
| Capsaicin | 0.025 to 0.25 wt. % |
| Capsicum | 0.025 to 0.25 wt. % |
| Capsicum Oleoresin | 0.025 to 0.25 wt. % |
| Glycol salicylate | 4.66 wt. % |
| Histamine dihydrochloride | 6X-30X in 1 mL |
| Menthol exceeding 1 wt. % | 1.25 to 16 wt. % |
| methyl nicotinate | 0.25 to 1 wt. % |
| Pectin | 2.8 mg-10 mg |
| Tannic acid | 1.5 wt. % |
| Tripelennamine hydrochloride | 0.5 to 2 wt. % |
| Trolamine salicylate (triethanolamine salicylate) | 10 wt. % |
| Turpentine oil | 6 to 50 wt. % |
| Zinc sulfate | 0.25 wt. % |
| Alcohol | 60 wt. %-70 wt. % (as isopropyl alcohol) |
| Alcohol, ethoxylated alkyl | |
| Benzalkonium chloride | 0.4 wt. %; 0.13 wt. % & 0.4 wt. % |
| Calamine | 1 to 25 wt. % |
| Ergot Fluid extract | |
| Ferric Chloride | |
| Panthenol | 0.01 wt. %; 0.2 wt. %; 0.5 wt. %; 0.6 wt. %; 1 wt. %; 1.125 wt. %; 1.5 wt. % |
| Peppermint oil | 0.1 wt. %; 0.08 wt. %; 0.34 wt. %; 1.95 wt. %; 6 wt. %; 8 wt. % As mentha oil-22.73 mg, 164.7 mg; |
| Pyrilamine Maleate | |
| sodium borate | 3X; 30X |
| Zinc oxide | 1 to 25 wt. % |
| Zirconium oxide | |
| Benzocaine | 5 wt. % to 20 wt. % |
| Ephedrine hydrochloride | 18 mg |
| Benzethonium chloride | 0.1 wt. %; 0.13 wt. %; 0.2 wt. %; 0.3 wt. % |
| Benzocaine | 5 to 20 wt. % |
| Bithionol | |
| Cetalkonium chloride | 0.01 wt. % |
| Chlorpheniramine maleate | 2 mg; 4 mg; 8 mg |
| Creosote, beechwood | 6X; 10X; 12X; 15X; 20X; 30C |
| Dexpanthenol | 0.2 wt. %; 0.3 wt. % |
| Diperodon hydrochloride | |
| Eucalyptus oil | 1 wt. %; 1.2 wt. %; 1.3 wt. %; 1.6 wt. % |
| Glycerin | 7 wt. % |
| Hectorite | |

TABLE D-continued

| ACTIVE | AMOUNT |
| --- | --- |
| Hydrogen peroxide | 0.6 wt. %; 1 wt. %; 1.5 wt. %; 3 wt. % |
| Impatiens biflora tincture | |
| Iron oxide | |
| Isopropyl alcohol | 60 wt. %-70 wt. % |
| Lanolin | 2 wt. %; 12.5 wt. %; 13 wt. %; 15 wt. %; 15.5 wt. %; 15.7 wt. %; 21.25 wt. %; 22 wt. %; 30 wt. %; 40 wt. %; 50 wt. % |
| Lead acetate (plumbum aceticum) | 6X; 12X; 6X-30X |
| Merbromin | |
| Mercuric chloride | 6X; 8X; 10X, 12X |
| Parethoxycaine hydrochloride | |
| Phenyltoloxamine dihydrogen citrate | 30 mg |
| Povidone-vinylacetate copolymers | |
| Salicylic acid | 0.5 wt. % to 2 wt. % |
| Simethicone | 125 mg; 250 mg |
| Sulfur | 3 wt. % to 10 wt. % |
| Zyloxin | |
| Allatoin | 0.5. to 2 wt. % |
| Aluminum acetate | 615 mg; 0.2 wt. %; 0.45 wt. % |
| Aluminum chloride hexahydrate | up to 15 wt. % |
| butamben picrate | 1 wt. % |
| cupric sulfate | 6X |
| dimethisoquin hydrochloride | 0.3 to 0.5 wt. % |
| diphenhydramine hydrochloride | 1 to 2 wt. % |
| hydrocrotisone | 0.25 to 0.5 wt. %; 0.5 to 1 wt. % |
| hydrocortisone acetate (0.25-0.5 wt. %) | 0.25 to 0.5 wt. %; 0.25 to 5 wt. % |
| menthol | 0.1 to 1 wt. % |
| Pramoxine hydrochloride | 0.5 to 1 wt. % |
| Resorcinol | 0.5 to 3 wt. % |
| Sodium bicarbonate | 1.916 g; 1.94 g; 2.452 g; 2.485 g |
| Topical starch | 10 to 98 wt. % |
| Trolamine (triethanolamine salicylate) | 10 wt. % |
| Zinc acetate | 0.1 to 2 wt. % |
| methyl salicylate | 10 to 60 wt. % |
| phenolate sodium | 0.5 to 1.5 wt. % |
| juniper tar | 1 to 5 wt. % |
| lidocaine | 0.5 to 4 wt. % |
| dyclonine hydrochloride | 0.5 to 1 wt. % |
| dibucaine hydrochloride | 0.25 to 1 wt. % |

Example 75

Method of Manufacturing a Topical Analgesic Cream

1. Dispense Hemp oil and CBD Isolate/Distillate into sterilized metal pan. Place on low heat and stir occasionally until all CBD has been fully dissolved into the hemp oil. Leave pan on low heat.
2. Dispense the following dry ingredients into a large sterilized metal pan: menthol, caffeine anhydrous white willow bark extract (salicin 98%), sodium benzoate, and tocopheryl acetate.
3. In a separate sterile container, dispense sodium bicarbonate.
4. In a separate sterile container, dispense carbopol 980 NF.
5. In a large mixing vessel, dispense the water.
6. Add the carbopol 980 NF to the water and mix with a high-speed mixer until all chunks have been evenly dispersed throughout the water.
7. In the container with the hemp Oil/CBD, remove from heat and dispense the lecithin and water for encapsulation.
8. Blend thoroughly with high speed mixer for 5 minutes.
9. Add the hemp mixture to the large metal pan containing the combined dry ingredients from step 2.
10. Blend the mixture of ingredients thoroughly.
11. Add contents of hemp mixture and dry ingredients into the large vessel containing the water/carbopol.
12. Blend for 3-5 minutes.
13. Gradually add sodium bicarbonate and blend at a high speed. Note: the volume of contents will expand with the addition of the sodium bicarbonate, be sure to allow at least ⅓ extra capacity in vessel to allow for this expansion.
14. Continue blending until all air bubbles are gone and consistency of cream appears fully homogenous.
15. Upon analysis of complete mixture of all ingredients, dispense the hemp pain cream into storage containers or into high viscosity liquid filler and primary packaging according to dosing specifications.

ENUMERATED EMBODIMENTS

Specific enumerated embodiments <1> to <208> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<1> A topical analgesic composition including the formulation of Example 1.

<2> A topical analgesic composition including the formulation of any one of Production Examples 2-73, further including a cannabinoid, terpene, flavonoid, or combination thereof.

<3> A topical analgesic composition including the formulation of any one of Production Examples 2-73, further including a cannabinoid obtained as a distillate from *cannabis*.

<4> A topical analgesic composition including the formulation of any one of Production Examples 2-73, further including a cannabinoid obtained as an extract from *cannabis*.

<5> A topical analgesic composition including the formulation of any one of Production Examples 2-73, further including a cannabinoid obtained as a resin from *cannabis*.

<6> A topical analgesic composition including the formulation of any one of Production Examples 2-73, further including a cannabinoid isolate obtained from *cannabis*.

<7> A topical analgesic composition including the formulation of any one of Production Examples 2-73, further including a cannabinoid obtained from *Cannabis indica*, *Cannabis ruderalis*, or *Cannabis sativa*.

<8> A topical analgesic composition including the formulation of any one of Production Examples 2-73, further including a cannabinoid present as an oil from *cannabis*.

<9> A topical analgesic composition including the formulation of any one of Production Examples 2-73, further including a cannabinoid present as hempseed oil.

<10> A topical analgesic composition including the formulation of anyone of Production Examples 2-73, further including a cannabinoid that is synthetically prepared.

<11> A topical analgesic composition including the formulation of anyone of Production Examples 2-73, further including a cannabinoid that is at least one of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

<12> A topical analgesic composition including the formulation of anyone of Production Examples 2-73, further including a cannabinoid that is at least one of CBD and THC.

<13> A topical analgesic composition including the formulation of any one of Production Examples 2-73, further including a terpene.

<14> A topical analgesic composition including the formulation of any one of Production Examples 2-73, further including a terpene that is a sesquiterpene.

<15> A topical analgesic composition including the formulation of anyone of Production Examples 2-73, further including a terpene obtained as a distillate from plant matter.

<16> A topical analgesic composition including the formulation of anyone of Production Examples 2-73, further including a terpene obtained as an extract from plant matter.

<17> A topical analgesic composition including the formulation of anyone of Production Examples 2-73, further including a terpene obtained as a resin from plant matter.

<18> A topical analgesic composition including the formulation of anyone of Production Examples 2-73, further including a terpene obtained from *Cannabis sativa, Syzygium aromaticum* (cloves), rosemary, or hops.

<19> A topical analgesic composition including the formulation of anyone of Production Examples 2-73, further including a terpene that is synthetically prepared.

<20> A topical analgesic composition including the formulation of any one of Production Examples 2-73, further including a terpene that is Beta-Caryophyllene.

<21> The topical analgesic of anyone of the above embodiments, wherein the amount of active ingredient expressed in terms of concentration (weight percent), present in the formulation of the any one of Production Examples 2-73, remains unchanged with the addition of the cannabinoid, terpene, flavonoid, or combination thereof. For Example, if the amount of active ingredient present in the formulation of the any one of Production Examples 2-73 is 1 wt. % lidocaine. With the addition of the cannabinoid, terpene, flavonoid, or combination thereof, the resulting amount of the lidocaine will remain at 1 wt. %.

<22> The topical analgesic of any one of the above embodiments, wherein the amount of inactive ingredient expressed in terms of concentration (weight percent), present in the formulation of the any one of Production Examples 2-73, decreases with the amount added of the cannabinoid, terpene, flavonoid, or combination thereof. For Example, if the amount of active ingredient present in the formulation of the any one of Production Examples 2-73 is 1 wt. % lidocaine, with the addition of the cannabinoid, terpene, flavonoid, or combination thereof, the resulting amount of the lidocaine will be less than 1 wt. %.

<23> The topical analgesic of any one of the above embodiments, wherein the aggregate amount of inactive ingredients, present in the formulation of the any one of Production Examples 2-73, decreases in proportion to the amount added of the cannabinoid, terpene, flavonoid, or combination thereof. For Example, if the aggregate amount of inactive ingredients present in the formulation of the any one of Production Examples 2-73 is 90 wt. %. With the addition of 1 wt. % of cannabinoid, terpene, flavonoid, or combination thereof, the resulting aggregate amount of those inactive ingredients will be 89 wt. %.

<24> The topical analgesic of any one of the above embodiments, wherein the aggregate amount of active ingredient and inactive ingredient in terms of concentration (weight percent), present in the formulation of the any one of Production Examples 2-73, decreases in proportion to the amount added of the cannabinoid, terpene, flavonoid, or combination thereof. For Example, the aggregate amount of active and inactive ingredients present in the formulation of the any one of Production Examples 2-73 is 100 wt. %. With the addition of 1 wt. % of cannabinoid, terpene, flavonoid, or combination thereof, the resulting aggregate amount of those active and inactive ingredients will be 99 wt. %.

<25> The topical analgesic of any one of the above embodiments, wherein the cannabinoid, terpene, flavonoid, or combination thereof, is present in an aggregate amount of up to 20 wt. %.

<26> The topical analgesic of any one of the above embodiments, wherein the cannabinoid, terpene, flavonoid, or combination thereof, is present in an aggregate amount of up to 10 wt. %.

<27> The topical analgesic of any one of the above embodiments, wherein the cannabinoid, terpene, flavonoid, or combination thereof, is present in an aggregate amount of up to 5 wt. %.

<28> The topical analgesic of any one of the above embodiments, wherein the cannabinoid, terpene, flavonoid, or combination thereof, is present in an aggregate amount of up to 1 wt. %.

<29> The topical analgesic of any one of the above embodiments, wherein the cannabinoid, terpene, flavonoid, or combination thereof, is present in an aggregate amount of up to 0.5 wt. %.

<30> The topical analgesic of any one of the above embodiments, wherein the cannabinoid, terpene, flavonoid, or combination thereof, is present in an aggregate amount of $0.330 \pm 0.1$ wt. %.

<31> The topical analgesic of anyone of the above embodiments, wherein the cannabinoid, terpene, flavonoid, or combination thereof, is present in an aggregate amount of 0.1 to 20 wt. %.

<32> The topical analgesic of any one of the above embodiments, wherein the cannabinoid, terpene, flavonoid, or combination thereof, is present in an aggregate amount of 0.1 to 10 wt. %.

<33> The topical analgesic of any one of the above embodiments, wherein the cannabinoid, terpene, flavonoid, or combination thereof, is present in an aggregate amount of 0.1 to 5 wt. %.

<34> The topical analgesic of any one of the above embodiments, wherein the cannabinoid, terpene, flavonoid, or combination thereof, is present in an aggregate amount of 0.01 to 2.5 wt. %.

<35> The topical analgesic of any one of the above embodiments, wherein the cannabinoid, terpene, flavonoid, or combination thereof, is present in an aggregate amount of 0.01 to 1 wt. %.

<36> The topical analgesic of any one of the above embodiments, wherein the cannabinoid, terpene, flavonoid, or combination thereof, is present in an aggregate amount of 0.01 to 0.5 wt. %.

<37> The topical analgesic of any one of the above embodiments, wherein the cannabinoid, terpene, flavonoid, or combination thereof, is present in an aggregate amount of 1 to 20 wt. %.

<38> The topical analgesic of any one of the above embodiments, wherein the cannabinoid, terpene, flavonoid, or combination thereof, is present in an aggregate amount of 1 to 10 wt. %.

<39> The topical analgesic of any one of the above embodiments, wherein the cannabinoid, terpene, flavonoid, or combination thereof, is present in an aggregate amount of 1 to 5 wt. %.

<40> The topical analgesic of any one of the above embodiments, wherein the cannabinoid, terpene, flavonoid, or combination thereof, is present in an aggregate amount of 0.05 to 2.5 wt. %.

<41> The topical analgesic of anyone of the above embodiments, wherein the cannabinoid, terpene, flavonoid, or combination thereof, is present in an aggregate amount of 0.05 to 1 wt. %.

<42> The topical analgesic of any one of the above embodiments, wherein the cannabinoid, terpene, flavonoid, or combination thereof, is present in an aggregate amount of 0.05 to 0.5 wt. %.

<43> The topical analgesic of any one of the above embodiments, which is in the form of a gel, pump gel, gel packet, cream, lotion, roll-on liquid, roll-on el, spray, pump spray, aerosol spray, stick, patch, ointment, liniment, or balm.

<44> A topical analgesic composition including the formulation of any one of Production Examples 2-73, further including a cannabinoid, terpene, flavonoid, or combination thereof; wherein the cannabinoid, terpene, flavonoid, or combination thereof, while present in the aggregate amounts, are characterized as inactive ingredients.

<45> A topical analgesic composition including the formulation of any one of Production Examples 2-73, further including a cannabinoid, terpene, flavonoid, or combination thereof; wherein the cannabinoid, terpene, flavonoid, or combination thereof, while present in the aggregate amounts, are characterized as an excipient.

<46> A topical analgesic composition including the formulation of any one of Production Examples 2-73, further including a cannabinoid, terpene, flavonoid, or combination thereof; wherein the cannabinoid, terpene, flavonoid, or combination thereof, while present in the aggregate amounts, are characterized as active ingredients.

<47> A topical analgesic composition including the formulation of any one of Production Examples 2-73, further including a cannabinoid, terpene, flavonoid, or combination thereof; wherein the cannabinoid terpene, flavonoid, or combination thereof, while present in the aggregate amounts, are characterized as an analgesic.

<48> A topical analgesic composition including one or more external analgesics of Production Example 74, further including a cannabinoid, terpene, flavonoid, or combination thereof, and a carrier system.

<49> A topical analgesic composition including one or more external analgesics of Production Example 74, further including a cannabinoid, and a carrier system.

<50> A topical analgesic composition including one or more external analgesics of Production Example 74, further including a cannabinoid obtained as a distillate from *cannabis*, and a carrier system.

<51> A topical analgesic composition including one or more external analgesics of Production Example 74, further including a cannabinoid obtained as an extract from *cannabis*, and a carrier system.

<52> A topical analgesic composition including one or more external analgesics of Production Example 74, further including a cannabinoid obtained as a resin from *cannabis*, and a carrier system.

<53> A topical analgesic composition including one or more external analgesics of Production Example 74, further including a cannabinoid isolate obtained from *cannabis*, and a carrier system.

<54> A topical analgesic composition including one or more external analgesics of Production Example 74, further including a cannabinoid obtained from *Cannabis* indica, *Cannabis ruderalis*, or *Cannabis sativa*, and a carrier system.

<55> A topical analgesic composition including one or more external analgesics of Production Example 74, further including a cannabinoid present as an oil from *cannabis*, and a carrier system.

<56> A topical analgesic composition including one or more external analgesics of Production Example 74, further including a cannabinoid present as hempseed oil, and a carrier system.

<57> A topical analgesic composition including one or more external analgesics of Production Example 74, further including a cannabinoid that is synthetically prepared, and a carrier system.

<58> A topical analgesic composition including one or more external analgesics of Production Example 74, further including a cannabinoid that is at least one of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran), and a carrier system.

<59> A topical analgesic composition including one or more external analgesics of Production Example 74, further including a cannabinoid that is at least one of CBD and THC, and a carrier system.

<60> A topical analgesic composition including one or more external analgesics of Production Example 74, further including a terpene, and a carrier system.

<61> A topical analgesic composition including one or more external analgesics of Production Example 74, further including a terpene that is a sesquiterpene, and a carrier system.

<62> A topical analgesic composition including one or more external analgesics of Production Example 74, further including a terpene obtained as a distillate from plant matter, and a carrier system.

<63> A topical analgesic composition including one or more external analgesics of Production Example 74, further including a terpene obtained as an extract from plant matter, and a carrier system.

<64> A topical analgesic composition including one or more external analgesics of Production Example 74, further including a terpene obtained as a resin from plant matter, and a carrier system.

<65> A topical analgesic composition including one or more external analgesics of Production Example 74, further including a terpene obtained from *Cannabis* sativa, *Syzygium aromaticum* (cloves), rosemary, or hops, and a carrier system.

<66> A topical analgesic composition including one or more external analgesics of Production Example 74, further including a terpene that is synthetically prepared, and a carrier system.

<67> A topical analgesic composition including one or more external analgesics of Production Example 74, further including a terpene that is Beta-Caryophyllene, and a carrier system.

<68> The topical analgesic of any one of the above embodiments, wherein the cannabinoid, terpene, flavonoid, or combination thereof, is present in an aggregate amount of up to 20 wt. %.

<69> The topical analgesic of any one of the above embodiments, wherein the cannabinoid, terpene, flavonoid, or combination thereof, is present in an aggregate amount of up to 10 wt. %.

<70> The topical analgesic of any one of the above embodiments, wherein the cannabinoid, terpene, flavonoid, or combination thereof, is present in an aggregate amount of up to 5 wt. %.

<71> The topical analgesic of anyone of the above embodiments, wherein the cannabinoid, terpene, flavonoid, or combination thereof, is present in an aggregate amount of up to 1 wt. %.

<72> The topical analgesic of any one of the above embodiments, wherein the cannabinoid, terpene, flavonoid, or combination thereof, is present in an aggregate amount of up to 0.5 wt. %.

<73> The topical analgesic of any one of the above embodiments, wherein the cannabinoid, terpene, flavonoid, or combination thereof, is present in an aggregate amount of 0.330±0.1 wt. %.

<74> The topical analgesic of any one of the above embodiments, wherein the cannabinoid, terpene, flavonoid, or combination thereof, is present in an aggregate amount of 0.1 to 20 wt. %.

<75> The topical analgesic of any one of the above embodiments, wherein the cannabinoid, terpene, flavonoid, or combination thereof, is present in an aggregate amount of 0.1 to 10 wt. %.

<76> The topical analgesic of any one of the above embodiments, wherein the cannabinoid terpene, flavonoid, or combination thereof, is present in an aggregate amount of 0.1 to 5 wt. %.

<77> The topical analgesic of any one of the above embodiments, wherein the cannabinoid, terpene, flavonoid, or combination thereof, is present in an aggregate amount of 0.01 to 2.5 wt. %.

<78> The topical analgesic of any one of the above embodiments, wherein the cannabinoid, terpene, flavonoid, or combination thereof, is present in an aggregate amount of 0.01 to 1 wt. %.

<79> The topical analgesic of any one of the above embodiments, wherein the cannabinoid, terpene, flavonoid, or combination thereof, is present in an aggregate amount of 0.01 to 0.5 wt. %.

<80> The topical analgesic of any one of the above embodiments, wherein the cannabinoid, terpene, flavonoid, or combination thereof, is present in an aggregate amount of 1 to 20 wt. %.

<81> The topical analgesic of anyone of the above embodiments, wherein the cannabinoid, terpene, flavonoid, or combination thereof, is present in an aggregate amount of 1 to 10 wt. %.

<82> The topical analgesic of any one of the above embodiments, wherein the cannabinoid, terpene, flavonoid, or combination thereof, is present in an aggregate amount of 1 to 5 wt. %.

<83> The topical analgesic of any one of the above embodiments, wherein the cannabinoid, terpene, flavonoid, or combination thereof, is present in an aggregate amount of 0.05 to 2.5 wt. %.

<84> The topical analgesic of any one of the above embodiments, wherein the cannabinoid, terpene, flavonoid, or combination thereof, is present in an aggregate amount of 0.05 to 1 wt. %.

<85> The topical analgesic of any one of the above embodiments, wherein the cannabinoid, terpene, flavonoid, or combination thereof, is present in an aggregate amount of 0.05 to 0.5 wt. %.

<86> The topical analgesic of any one of the above embodiments, which is in the form of a gel, pump gel, gel packet, cream, lotion, roll-on liquid, roll-on gel, spray, pump spray, aerosol spray, stick, patch, ointment, liniment, or balm.

<87> A topical analgesic composition including one or more external analgesics of Production Example 74, further including a cannabinoid, terpene, flavonoid, or combination thereof, and a carrier system; wherein the cannabinoid, terpene, flavonoid, or combination thereof, while present in the aggregate amounts, are characterized as inactive ingredients.

<88> A topical analgesic composition including one or more external analgesics of Production Example 74, further including a cannabinoid, terpene, flavonoid, or combination thereof, and a carrier system; wherein the cannabinoid, terpene, flavonoid, or combination thereof, while present in the aggregate amounts, are characterized as an excipient.

<89> A topical analgesic composition including one or more external analgesics of Production Example 74, further including a cannabinoid, terpene, flavonoid, or combination thereof, and a carrier system; wherein the cannabinoid, terpene, flavonoid, or combination thereof, while present in the aggregate amounts, are characterized as active ingredients.

<90> A topical analgesic composition including one or more external analgesics of Production Example 74, further including a cannabinoid, terpene, flavonoid, or combination thereof, and a carrier system; wherein the cannabinoid, terpene, flavonoid, or combination thereof, while present in the aggregate amounts, are characterized as an analgesic.

<91> The topical analgesic of anyone of the above embodiments, which is in the form of a cream, gel, lotion, patch, liniment, spray, roll-on, stick, or balm.

<92> A topical analgesic cream that includes:
   solvent,
   external analgesic,
   emulsifier.
   polymeric binder,
   solubility oil,
   cannabinoid,
   anti-oxidant, and
   preservative.

<93> The topical analgesic cream of embodiment <92>, wherein the solvent includes at least one of water, glycerin, propylene glycol, propanediol, butylene glycol, ethoxydiglycol, isododecane, isohexadecane, octyldodecanol, hexylene glycol, 1,2-hexanediol, and dicaprylyl carbonate.

<94> The topical analgesic cream of embodiment <92>, wherein the solvent includes water.

<95> The topical analgesic cream of embodiment <92>, wherein the solvent is present in 88±5 wt. %.

<96> The topical analgesic cream of embodiment <92>, wherein the solvent includes 88±5 wt. % water.

<97> The topical analgesic cream of any one of embodiments <92> to <96>, wherein the external analgesic includes menthol.

<98> The topical analgesic cream of any one of embodiments <92> to <96>, wherein the external analgesic includes menthol.

<99> The topical analgesic cream of any one of embodiments <92> to <98>, wherein the external analgesic is present in 2.5±0.5 wt. %.

<100> The topical analgesic cream of any one of embodiments <92> to <98>, wherein the external analgesic includes 2.5±0.5 wt. % menthol.

<101> The topical analgesic cream of any one of embodiments <92> to <96>, wherein the external analgesic includes at least one of: menthol, trolamine salicylate, camphor, capsaicin, lidocaine HCl, lidocaine, and methyl salicylate.

<102> The topical analgesic cream of any one of embodiments <92> to <96>, wherein the external analgesic includes at least one of: 0.75-16 wt. % menthol, 10±2 wt. % trolamine salicylate, 2-11 wt. % camphor, 0.025-0.15 wt. % capsaicin, 4±0.8 wt. % lidocaine HCl, 4±0.8 wt. % lidocaine, and 10-30 wt. % methyl salicylate.

<103> The topical analgesic cream of any one of embodiments <92> to <96>, wherein the external analgesic includes:
  2-16 wt. % menthol,
  10±2 wt. % trolamine salicylate,
  3.1±0.7 wt. % camphor,
  0.025-0.15 wt. % capsaicin,
  4±0.8 wt. % lidocaine HCl,
  4±0.8 wt. % lidocaine,
  4-11 wt. % camphor and 8-16 wt. % menthol,
  0.025 wt. % capsaicin and 10±2 wt. % menthol,
  3-10 wt. % menthol and 15-30 wt. % methyl salicylate,
  4±0.8 wt. % lidocaine HCl and 1±0.25 wt. % menthol, or
  3-7 wt. % camphor, 5-16 wt. % menthol, and 10-30 wt. % methyl salicylate.

<104> The topical analgesic cream of any one of embodiments <92> to <96>, wherein the external analgesic includes:
  2 wt. % menthol,
  2.5 wt. % menthol,
  4 wt. % menthol,
  5 wt. % menthol,
  7 wt. % menthol,
  7.5 wt. % menthol,
  10 wt. % menthol,
  10.5 wt. % menthol,
  16 wt. % menthol,
  10% trolamine salicylate,
  3.1 wt. % camphor.
  0.025 wt. % capsaicin,
  0.035 wt. % capsaicin,
  0.1 wt. % capsaicin,
  0.15 wt. % capsaicin,
  4 wt. % lidocaine HCl,
  4 wt. % lidocaine,
  11 wt. % camphor and 16 wt. % menthol,
  4 wt % camphor and 16 wt. % menthol,
  11 wt. % camphor and 11 wt. % menthol,
  11 wt. % camphor and 10 wt. % menthol,
  11 wt. % camphor and 8 wt % menthol,
  0.025 wt. % capsaicin and 10 wt. % menthol,
  10 wt. % menthol and 15 wt. % methyl salicylate,
  10 wt. % menthol and 30 wt. % methyl salicylate
  7.6 wt. % menthol, and 29 wt. % methyl salicylate,
  8 wt. % menthol and 16 wt % methyl salicylate,
  16 wt. % menthol and 28 wt. % methyl salicylate,
  3 wt % menthol and 10 wt. % methyl salicylate,
  4 wt. % lidocaine HC and 1 wt. % menthol,
  4 wt. % camphor, 10 wt. % menthol, and 30 wt % methyl salicylate,
  3 wt. % camphor, 5 wt. % menthol, and 15 wt. % methyl salicylate,
  7 wt. % camphor, 16 wt. % menthol, and 25 wt. % methyl salicylate, or
  3.1 wt. % camphor, 16 wt. % menthol, and 10 wt. % methyl salicylate.

<105> The topical analgesic cream of any one of embodiments <92> to <104>, wherein the emulsifier includes at least one of polysorbate 60, laureth-4, potassium cetyl sulfate, cetyl alcohol, cetearyl alcohol, stearyl alcohol, glyceryl stearate, propylene glycol, polyglyceryl-6 laurate, ceteareth-20, PEG-100 stearate, sodium lauroyl lactylate, myristyl myristate, carbomer, polysorbate 80, polawax, sorbitan stearate, gum Arabic, *brassica* alcohol, carbomer 980 QD, sodium stearate, polyhydroxystearic acid, PEG-150 distearate, glyceryl oleate, emulsifying wax, glyceryl monooleate, phospholipids, polyoxyethylene alkyl ethers, polyoxyethylene, castor oil derivatives, sorbitan fatty acid esters, polyoxyethylene stearates, polyoxylglycerides, polysorbate, sorbitan esters, and lecithin.

<106> The topical analgesic cream of any one of embodiments <92> to <105>, wherein the emulsifier is present in 2±0.4 wt. %.

<107> The topical analgesic cream of any one of embodiments <92> to <104>, wherein the emulsifier includes lecithin.

<108> The topical analgesic cream of any one of embodiments <92> to <104>, wherein the emulsifier includes 2±0.4 wt. % lecithin.

<109> The topical analgesic cream of any one of embodiments <92> to <108>, wherein the polymeric binder includes at least one of Carbopol 980, carbomer, cetyl alcohol, stearic acid, carnauba wax, hydroxyethyl cellulose, guar gum, xanthan gum, gelatin, magnesium aluminum silicate, silica, bentonite, cetyl palmitate, ammonium acryloyldimethyltaurate, cetearyl alcohol, glucose-D, hectorite gel, stearyl palmitate, gum arabic, hydroxypropyl starch phosphate, tapioca starch, acrylates octylacrylamide copolymer, carbomer 940, polyamide 3, castor wax, hydroxypropyl methylcellulose, *Caesalpinia spinosa* gum, *brassica* alcohol, carbomer 980 QD, sodium stearate, polyhydroxystearic acid, tribehenin, arrowroot starch, rice starch, candelilla wax, beeswax ozokerite wax, sunflower wax, PEG-150 distearate, polyacrylate crosspolymer-6, acrylates C10-30 alkyl acrylate crosspolymer, hydroxypropyl guar, and cyclopentasiloxane (silicone gel).

<110> The topical analgesic cream of any one of embodiments <92> to <108>, wherein the polymeric binder includes Carbopol 980.

<111> The topical analgesic cream of any one of embodiments <92> to <108>, wherein the polymeric binder is present in 1.4±0.28 wt. %.

<112> The topical analgesic cream of any one of embodiments <92> to <108>, wherein the polymeric binder includes 1.4 t 0.28 wt. % Carbopol 980.

<113> The topical analgesic cream of any one of embodiments <92> to <112>, wherein the solubility oil is a solubility oil for a cannabinoid.

<114> The topical analgesic cream of any one of embodiments <92> to <112>, wherein the solubility oil is a solubility oil for a cannabinoid isolate.

<115> The topical analgesic cream of any one of embodiments <92> to <112>, wherein the solubility oil is a solubility oil for a CBD isolate.

<116> The topical analgesic cream of any one of embodiments <92> to <112>, wherein the solubility oil includes hemp oil.

<117> The topical analgesic cream of any one of embodiments <92> to <112>, wherein the solubility oil is present in 1±0.2 wt. %.
<118> The topical analgesic cream of any one of embodiments <92> to <112>, wherein the solubility oil includes organic hemp oil.
<119> The topical analgesic cream of any one of embodiments <92> to <112>, wherein the solubility oil includes 1±0.2 wt. % organic hemp oil.
<120> The topical analgesic cream of any one of embodiments <92> to <119>, wherein the cannabinoid is in the form of hemp extract.
<121> The topical analgesic cream of any one of embodiments <92> to <119>, wherein the cannabinoid includes 0.32±0.08 wt. % hemp extract.
<122> The topical analgesic cream of any one of embodiments <92> to <119>, wherein the cannabinoid is present in up to 2 wt %.
<123> The topical analgesic cream of any one of embodiments <92> to <119>, wherein the cannabinoid is present in up to 1 wt. %.
<124> The topical analgesic cream of any one of embodiments <92> to <119>, wherein the cannabinoid is present in up to 0.5 wt. %.
<125> The topical analgesic cream of any one of embodiments <92> to <119>, wherein the cannabinoid is present in 0.1 to 0.5 wt. %.
<126> The topical analgesic cream of any one of embodiments <92> to <119>, wherein the cannabinoid is present in 0.3±0.15 wt. %.
<127> The topical analgesic cream of any one of embodiments <92> to <119>, wherein the cannabinoid is present in 0.3±0.1 wt. %.
<128> The topical analgesic cream of any one of embodiments <92> to <119>, wherein the cannabinoid is present in 0.32±0.08 wt. %.
<129> The topical analgesic cream of any one of embodiments <92> to <128>, wherein the anti-oxidant includes at least one of tocopherol (vitamin E), tocopheryl acetate (vitamin E acetate), anthocyanins, proanthocyanins, alpha-lipoic acid, catechins, retinol (vitamin A), beta-carotene (vitamin A), Coenzyme Q10, chlorogenic acid, curcumin, vitamin C, theograndin, luteolin, acetophenone derivatives, monoterpenes, sesquiterpenes, triterpenes, phytosterols, ferulic acid, and lycopene.
<130> The topical analgesic cream of any one of embodiments <92> to <128>, wherein the anti-oxidant is present in 0.1±0.02 wt. %.
<131> The topical analgesic cream of any one of embodiments <92> to <128>, wherein the anti-oxidant includes tocopheryl acetate.
<132> The topical analgesic cream of any one of embodiments <92> to <128>, wherein the anti-oxidant includes 0.1±0.02 wt. % tocopheryl acetate.
<133> The topical analgesic cream of any one of embodiments <92> to <132>, wherein the preservative includes at least one of butylparaben, ethylparaben, methylparaben, propylparaben, sorbic acid, benzyl alcohol, salicylic acid, formaldehyde, tetrasodium ethylenediaminetetra-acetic acid (EDTA), neroli hydrosol, phenoxyethanol, ethylhexylglycerin, methylisothiazolinone, methylchloroisothiazolinone, citric acid, sodium benzoate, and tetrasodium glutamate diacetate.
<134> The topical analgesic cream of any one of embodiments <92> to <132>, wherein the preservative is present in 0.1±0.02 wt. %.
<135> The topical analgesic cream of any one of embodiments <92> to <132>, wherein the preservative includes sodium benzoate.
<136> The topical analgesic cream of any one of embodiments <92> to <132>, wherein the preservative includes 0.1±0.02 wt. % sodium benzoate.
<137> The topical analgesic cream of any one of embodiments <92> to <136>, that further includes a microcirculation stimulant.
<138> The topical analgesic cream of any one of embodiments <92> to <136>, that further includes caffeine.
<139> The topical analgesic cream of any one of embodiments <92> to <136>, that further includes caffeine as a microcirculation stimulant.
<140> The topical analgesic cream of any one of embodiments <92> to <136>, that further includes 1.5±0.3 wt. % caffeine as a microcirculation stimulant.
<141> The topical analgesic cream of any one of embodiments <92> to <136>, that further includes 1.5±0.3 wt. % microcirculation stimulant.
<142> The topical analgesic cream of any one of embodiments <92> to <141>, that further includes a pH adjusting agent.
<143> The topical analgesic cream of any one of embodiments <92> to <141>, that further includes sodium bicarbonate as a pH adjusting agent.
<144> The topical analgesic cream of any one of embodiments <92> to <141>, that further includes 1.5±0.3 wt. % sodium bicarbonate as a pH adjusting agent.
<145> The topical analgesic cream of any one of embodiments <92> to <141>, that further includes 1.5±0.3 wt. % pH adjusting agent.
<146> The topical analgesic cream of any one of embodiments <92> to <145>, that further includes a herbal active ingredient.
<147> The topical analgesic cream of any one of embodiments <92> to <145>, that further includes a herbal active ingredient that is a natural topical pain remedy.
<148> The topical analgesic cream of any one of embodiments <92> to <145>, that further includes 1.25±0.25 wt. % herbal active ingredient that is a natural topical pain remedy.
<149> The topical analgesic cream of any one of embodiments <92> to <145>, that further includes white willow bark extract as a herbal active ingredient.
<150> The topical analgesic cream of any one of embodiments <92> to <145>, that further includes 1.25±0.25 wt. % white willow bark extract as a herbal active ingredient.
<151> The topical analgesic cream of any one of embodiments <92> to <145>, that further includes salicin as a herbal active ingredient, wherein the salicin is present as white willow bark extract.
<152> The topical analgesic cream of any one of embodiments <92> to <145>, that further includes 1.25±0.25 wt. % salicin as a herbal active ingredient, wherein the salicin is present as white willow bark extract.
<153> A topical analgesic cream that includes:
menthol,
cannabidiol (CBD),
carbopol,
lecithin,
caffeine anhydrous,
salicin,
organic hemp oil,
sodium benzoate,
tocopheryl acetate,
sodium bicarbonate, and
water.

‹154› The topical analgesic cream of embodiment ‹153›, wherein the menthol is present in 2.5±0.5 wt. %.

‹155› The topical analgesic cream of embodiment ‹153›, wherein the cannabidiol (CBD) is present as 0.32±0.08 wt. % organic hemp extract or 0.35±0.08 wt. % organic hemp extract.

‹156› The topical analgesic cream of any one of embodiments ‹153› to ‹155›, wherein the carbopol is present in 1.4±0.3 wt. %.

‹157› The topical analgesic cream of any one of embodiments ‹153› to ‹156›, wherein the lecithin is present in 2±0.4 wt. %.

‹158› The topical analgesic cream of any one of embodiments ‹153› to ‹157›, wherein the caffeine anhydrous is present in 1.5±0.3 wt. %.

‹159› The topical analgesic cream of any one of embodiments ‹153› to ‹158›, wherein the salicin is present as white willow bark extract, in 1.25±0.25 wt %.

‹160› The topical analgesic cream of any one of embodiments ‹153› to ‹159›, wherein the organic hemp oil is present in 1±0.2 wt. %.

‹161› The topical analgesic cream of any one of embodiments ‹153› to ‹160›, wherein the sodium benzoate is present in 0.1±0.02 wt. %.

‹162› The topical analgesic cream of any one of embodiments ‹153› to ‹161›, wherein the tocopheryl acetate is present in 0.1±0.04 wt %.

‹163› The topical analgesic cream of any one of embodiments ‹153› to ‹162›, wherein the sodium bicarbonate is present in 1.5±0.3 wt. %.

‹164› The topical analgesic cream of any one of embodiments ‹153› to ‹163›, wherein the water is present in 88.33±5 wt. % or 88.30±5 wt. %.

‹165› The topical analgesic cream of any one of embodiments ‹153› to ‹164›, having a total THC content of less than 0.05 mg/mL, wherein the total THC content is defined as the amount of THCA/mL*0.877, plus the amount of THC/mL*1, expressed as:

Total THC content=(amount of THCA/mL*0.877)+ (amount of THC/mL*1)<0.05 mg/mL

‹166› The topical analgesic cream of any one of embodiments ‹153› to ‹164›, having a total THC content of less than 0.025 mg/mL, wherein the total THC content is defined as the amount of THCA/mL*0.877, plus the amount of THC/mL*1, expressed as:

Total THC content=(amount of THCA/mL*0.877)+ (amount of THC/mL*1)<0.025 mg/mL

‹167› The topical analgesic cream of any one of embodiments ‹153› to ‹164›, substantially free from (a)-(e):
  (a) Tetrahydrocannabinol (THC),
  (b) Tetrahydrocannabinolic Acid (THCA),
  (c) Cannabidiolic Acid (CBDA),
  (d) Cannabinol (CBN),
  (e) Cannabigerol (CBG),
such that any of (a)-(e) present in the topical analgesic cream is present such that the topical analgesic cream includes each in no more than 0.01 mg/mL.

‹168› The topical analgesic cream of any one of embodiments ‹153› to ‹164›, substantially free from (a)-(e):
  (a) Tetrahydrocannabinol (THC),
  (b) Tetrahydrocannabinolic Acid (THCA),
  (c) Cannabidiolic Acid (CBDA),
  (d) Cannabinol (CBN),
  (e) Cannabigerol (CBG),
such any one or more of (a)-(e) that is present in the topical analgesic cream is present in a total, aggregate amount of no more than 0.02 mg/mL.

‹169› A topical analgesic cream that includes:
  2.5±0.5 wt. % menthol,
  0.35±0.08 wt. % cannabidiol (CBD),
  1.4±0.3 wt. % carbopol 980 NF,
  2±0.4 wt. % lecithin,
  1.5±0.3 wt. % caffeine anhydrous,
  1.25±0.25 wt. % salicin (98 wt. % pure),
  1±0.2 wt. % organic hemp oil,
  0.1±0.02 wt. % sodium benzoate,
  0.1±0.02 wt. % tocopheryl acetate,
  1.5±0.3 wt. % sodium bicarbonate, and
  88.30±5 wt. % water.

‹170› The topical analgesic cream of embodiment ‹169›, formulated as 30±10 mL viscous cream and contained within an airless pump bottle with a protective cap and a pump lid.

‹171› A topical analgesic cream that includes:
  2.5±0.5 wt. % menthol,
  0.32±0.08 wt. % cannabidiol (CBD),
  1.4±0.3 wt. % carbopol 980 NF,
  2±0.4 wt. % lecithin,
  1.5±0.3 wt. % caffeine anhydrous,
  1.25±0.25 wt. % salicin (98 wt. % pure),
  1±0.2 wt. % organic hemp oil,
  0.1±0.02 wt % sodium benzoate,
  0.1±0.02 wt. % tocopheryl acetate,
  1.5±0.3 wt. % sodium bicarbonate, and
  88.33±5 wt. % water.

‹172› The topical analgesic cream of anyone of embodiments ‹92› to ‹171›, formulated as 50±15 mL viscous cream and contained within an airless pump bottle with a protective cap and a pump lid.

‹173› A method that includes topically administering to a subject the topical analgesic of any one of the above embodiments.

‹174› A method for the temporary relief of minor aches and pains of muscles and joints, the method includes topically administering to the affected areas of a subject in need thereof the topical analgesic of any one of embodiments ‹1› to ‹173›.

‹175› The method of embodiment ‹174›, wherein the minor aches and pains of muscles and joints is associated with at least one of simple backache, sore muscles, muscle fatigue, muscle stiffness, joint stiffness, arthritis, muscle strains, bursitis, tendonitis, bruises, contusion, cramps, and sprain.

‹176› The method of any one of embodiments ‹173› to ‹175›, wherein the topical analgesic provides a cooling sensation.

‹177› The method of any one of embodiments ‹173› to ‹175›, wherein the topical analgesic provides cooling pain relief.

‹178› The method of any one of embodiments ‹173› to ‹175›, wherein the topical analgesic provides warming pain relief.

‹179› The method of any one of embodiments ‹173› to ‹175›, wherein the topical analgesic provides a warming sensation.

‹180› The method of any one of embodiments ‹173› to ‹179›, wherein the topical analgesic soothes muscle aches and pains.

‹181› The method of any one of embodiments ‹173› to ‹180›, wherein the topical analgesic alleviates discomfort resulting from strenuous athletic training.

<182> The method of any one of embodiments <173> to <181>, wherein the topical analgesic aids in recovery from strenuous athletic training.
<183> The method of any one of embodiments <173> to <182>, wherein the topical analgesic numbs away the pain.
<184> The method of any one of embodiments <173> to <183>, wherein the topical analgesic desensitizes aggravated nerves.
<185> The method of any one of embodiments <173> to <184>, wherein the topical analgesic is applied to a clean and dry topical skin surface of the subject.
<186> The method of any one of embodiments <173> to <185>, wherein the topical analgesic is applied to at least one of the back, neck, shoulder, knee, elbow, foot, ankle, leg arm, hand, and wrist of the subject.
<187> The method of any one of embodiments <173> to <186>, wherein the topical analgesic is applied up to four times a day.
<188> The method of any one of embodiments <173> to <187>, further including after topically administering the topical analgesic to the subject, rubbing or massaging the topical analgesic over the affected areas until thoroughly absorbed into the skin.
<189> The method of any one of embodiments <173> to <188>, wherein the subject is at least 12 years old.
<190> The method of any one of embodiments <173> to <188>, wherein the subject is at least 18 years old.
<191> The method of any one of embodiments <173> to <190>, wherein the subject is a human.
<192> The method of any one of embodiments <173> to <191>, wherein after administering to a topical skin surface, the hands are washed with soap and water.
<193> A method including:
  (a) dissolving CBD in hemp oil to obtain a hemp mixture;
  (b) contacting menthol, caffeine anhydrous, white willow bark extract (salicin 98%), sodium benzoate, and tocopheryl acetate to obtain a dry mixture;
  (c) contacting Carbopol 980 NF and water until the Carbopol 980 NF is dissolved in the water or is dispersed throughout the water, to obtain a Carbopol mixture;
  (d) contacting lecithin, water, and the dissolved CBD to form a first mixture;
  (e) contacting the hemp mixture, the dry mixture, and the Carbopol mixture to form a second mixture;
  (f) contacting sodium bicarbonate and the second mixture.
<194> The method of embodiment <193>, which is a method for forming a cream.
<195> The method of embodiment <194>, which is a method for forming a topical analgesic cream.
<196> The method of any one of embodiments <193> to <195>, wherein the CBD is present as a CBD distillate, a CBD isolate, or a combination thereof.
<197> The method of any one of embodiments <193> to <196>, wherein the dissolving of the CBD in the hemp oil is carried out at a temperature above 25° C.
<198> The method of any one of embodiments <193> to <197>, wherein the dissolving of the CBD in the hemp oil is carried out at a temperature of 25-100° C.
<199> The method of any one of embodiments <193> to <198>, wherein the contacting of the menthol, the caffeine anhydrous, the white willow bark extract (salicin 98%), the sodium benzoate, and the tocopheryl acetate to obtain the dry mixture.
<200> The method of any one of embodiments <193> to <199>, wherein the contacting of the Carbopol 980 NF the water is carried out with a high-speed mixer.
<201> The method of any one of embodiments <193> to <200>, wherein the first mixture is an encapsulated mixture.
<202> The method of any one of embodiments <193> to <201>, wherein the first mixture is an encapsulated mixture including the lecithin, the water, and the dissolved CBD.
<203> The method of any one of embodiments <193> to <202>, wherein the contacting of the lecithin, the water, and the dissolved CBD is carried out with a high speed mixer.
<204> The method of any one of embodiments <193> to <203>, wherein the contacting of the hemp mixture, the dry mixture, and the Carbopol mixture to firm a second mixture is carried out with a high speed mixer.
<205> The method of any one of embodiments <193> to <204>, wherein the contacting of the sodium bicarbonate and the second mixture is carried out while blending.
<206> The method of any one of embodiments <193> to <205>, wherein the contacting of the sodium bicarbonate and the second mixture is carried out while blending at a high speed, until substantially no air bubbles are present.
<207> The method of any one of embodiments <193> to <206>, wherein the contacting of the sodium bicarbonate and the second mixture is carried out while blending at a high speed, until the consistency of a cream is obtained.
<208> The method of any one of embodiments <193> to <207>, wherein the contacting of the sodium bicarbonate and the second mixture is carried out while blending at a high speed, until a substantially homogenous consistency is achieved.

The invention claimed is:

1. A method for the temporary relief of aches or pains of affected muscles or joints areas, the method comprising topically administering to the affected areas of a subject in need thereof a topical analgesic cream comprising:
    menthol,
    cannabidiol (CBD),
    carbopol,
    lecithin,
    caffeine anhydrous,
    a salicylic compound consisting of salicin (98 wt. % pure),
    organic hemp oil,
    sodium benzoate,
    tocopheryl acetate,
    sodium bicarbonate, and
    water.

2. The method of claim 1, wherein the aches or pains of affected muscles or joints areas are associated with at least one of: simple backache, sore muscles, muscle fatigue, muscle stiffness, joint stiffness, arthritis, muscle strains, bursitis, tendonitis, bruises, contusion, cramps, and sprain.

3. The method of claim 1, wherein the topical analgesic cream provides a cooling sensation.

4. The method of claim 1, wherein the topical analgesic cream provides cooling pain relief.

5. The method of claim 1, wherein the topical analgesic cream alleviates discomfort resulting from strenuous athletic training.

6. The method of claim 1, wherein the topical analgesic cream aids in recovery from strenuous athletic training.

7. The method of claim 1, wherein the topical analgesic cream is applied to a clean and dry topical skin surface of the subject.

8. The method of claim 1, wherein the topical analgesic cream is applied to at least one of the back, neck, shoulder, knee, elbow, foot, ankle, leg, arm, hand, and wrist of the subject.

9. The method of claim 1, wherein the cannabidiol (CBD) is obtained from *cannabis* as a CBD Isolate (99 wt. % pure).

10. The method of claim 1, wherein the topical analgesic cream is applied up to four times a day.

11. The method of claim 1, further comprising after topically administering the topical analgesic cream to the subject, rubbing or massaging the topical analgesic cream over the affected areas until thoroughly absorbed into the skin.

12. The method of claim 1, wherein the menthol is present in 2.5±0.5 wt. %.

13. The method of claim 1, wherein the cannabidiol (CBD) is present in 0.33±0.07 wt. %.

14. The method of claim 1, wherein the caffeine anhydrous is present in 1.5±0.3 wt. %.

15. The method of claim 1, wherein the salicin is present in 1.25±0.25 wt. %.

16. The method of claim 1, wherein the organic hemp oil is present in 1±0.2 wt. %.

17. The method of claim 1, wherein the tocopheryl acetate is present in 0.2±0.04 wt. %.

18. The method of claim 1, wherein the topical analgesic cream further comprises a terpene.

19. The method of claim 1, wherein the topical analgesic cream further comprises a terpene that is a sesquiterpene.

20. A method for the temporary relief of aches or pains of affected muscles or joints areas, the method comprising topically administering to the affected areas of a subject in need thereof a topical analgesic cream comprising:
- 2.5±0.5 wt. % menthol,
- 0.33±0.1 wt. % cannabidiol (CBD),
- 1.4±0.3 wt. % carbopol 980 NF,
- 2±0.4 wt. % lecithin,
- 1.5±0.3 wt. % caffeine anhydrous,
- 1.25±0.25 wt % salicylic compound consisting of salicin (98 wt. % pure),
- 1±0.2 wt. % organic hemp oil,
- 0.1±0.02 wt. % sodium benzoate,
- 0.2±0.04 wt. % tocopheryl acetate,
- 1.5±0.3 wt. % sodium bicarbonate, and
- 88.22±5 wt. % water;

wherein, the cannabidiol (CBD) is obtained from *cannabis* as a CBD Isolate (99 wt. % pure); and the aches or pains of affected muscles or joints areas are associated with at least one of: simple backache, sore muscles, muscle fatigue, muscle stiffness, joint stiffness, arthritis, muscle strains, bursitis, tendonitis, bruises, contusion, cramps, and sprain.

* * * * *